United States Patent
Pedersen et al.

(10) Patent No.: US 9,924,281 B2
(45) Date of Patent: Mar. 20, 2018

(54) BINAURAL HEARING ASSISTANCE SYSTEM COMPRISING TWO WIRELESS INTERFACES

(71) Applicant: Oticon A/S, Smørum (DK)

(72) Inventors: Michael Syskind Pedersen, Smørum (DK); Jesper Jensen, Smørum (DK); Peter S. K. Hansen, Smørum (DK); Bjarne Kielsholm-Ribalaygua, Smørum (DK); Kåre Tais Christensen, Smørum (DK); Jens Troelsen, Smørum (DK); Hans Christian Schott, Smørum (DK); Rune Sø, Smørum (DK)

(73) Assignee: OTICON A/S, Smørum (DK)

(*) Notice: Subject to any disclaimer, the term of this patent is extended or adjusted under 35 U.S.C. 154(b) by 0 days.

(21) Appl. No.: 15/620,149

(22) Filed: Jun. 12, 2017

(65) Prior Publication Data
US 2017/0280256 A1    Sep. 28, 2017

Related U.S. Application Data

(63) Continuation of application No. 14/534,282, filed on Nov. 6, 2014, now Pat. No. 9,712,927.

(30) Foreign Application Priority Data

Nov. 7, 2013  (EP) ..................... 13191944

(51) Int. Cl.
*H04R 5/00* (2006.01)
*H04R 25/00* (2006.01)

(52) U.S. Cl.
CPC ..... *H04R 25/552* (2013.01); *H04R 2205/041* (2013.01); *H04R 2225/51* (2013.01); *H04R 2225/55* (2013.01); *H04R 2460/03* (2013.01)

(58) Field of Classification Search
CPC .............. H04R 25/552; H04R 2225/55; H04R 2460/03; H04R 2225/51; H04R 2205/041
(Continued)

(56) References Cited

U.S. PATENT DOCUMENTS

2005/0110700 A1   5/2005  Terry
2005/0255843 A1  11/2005  Hilpisch et al.
(Continued)

FOREIGN PATENT DOCUMENTS

EP    1 107 472 A2   6/2001
EP    1 777 644 A1   4/2007
(Continued)

*Primary Examiner* — Paul S Kim
(74) *Attorney, Agent, or Firm* — Birch, Stewart, Kolasch & Birch, LLP

(57) ABSTRACT

The application relates to a binaural hearing assistance system comprising first and second hearing assistance devices adapted for being located at or in left and right ears of a user. The application further relates to a method of operating a binaural hearing assistance system. The object of the present application is to provide an improved binaural hearing assistance system. The problem is solved in that each of the first and second hearing assistance devices comprises a) a first wireless interface comprising first antenna and transceiver circuitry adapted for establishing a first communication link to the respective other hearing assistance device based on near-field communication; b) a second wireless interface comprising second antenna and transceiver circuitry adapted for establishing a second communication link to an auxiliary device based on far-field communication; c) a link control unit operatively coupled to the second antenna and transceiver circuitry and configured to repeatedly provide a second link quality measure indicative of a link quality of the second communication link; wherein the first and second hearing assistance devices are configured to exchange said respective second link quality (Continued)

measures between them via said first and/or second communication links. This has the advantage of providing a robust and flexible system. The invention may e.g. be used for binaural hearing assistance systems, e.g. binaural hearing aid systems, where audio quality and power consumption has to be mutually optimized.

17 Claims, 7 Drawing Sheets

(58) Field of Classification Search
USPC ........................................................ 381/23.1
See application file for complete search history.

(56) References Cited

U.S. PATENT DOCUMENTS

| | | |
|---|---|---|
| 2007/0291970 A1 | 12/2007 | Nikles et al. |
| 2008/0159548 A1 | 7/2008 | Solum |
| 2010/0021176 A1 | 1/2010 | Holcombe et al. |
| 2010/0128907 A1 | 5/2010 | Dijkstra et al. |
| 2010/0184383 A1* | 7/2010 | Lerke .................. H04R 25/552 455/66.1 |
| 2011/0222621 A1 | 9/2011 | Christensen et al. |
| 2013/0195300 A1 | 8/2013 | Larsen et al. |

FOREIGN PATENT DOCUMENTS

| | | |
|---|---|---|
| EP | 2 211 579 A1 | 7/2010 |
| WO | WO 2005/053179 A1 | 6/2005 |
| WO | WO 2005/055654 A1 | 6/2005 |

* cited by examiner

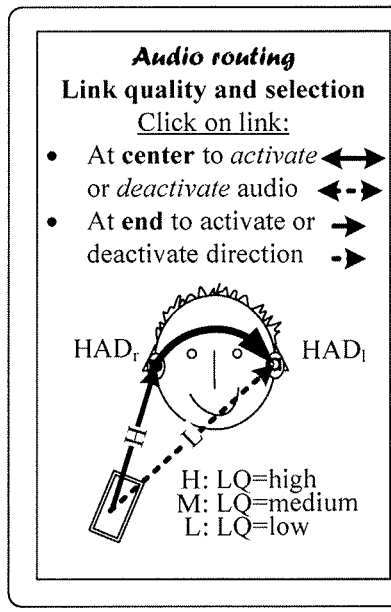 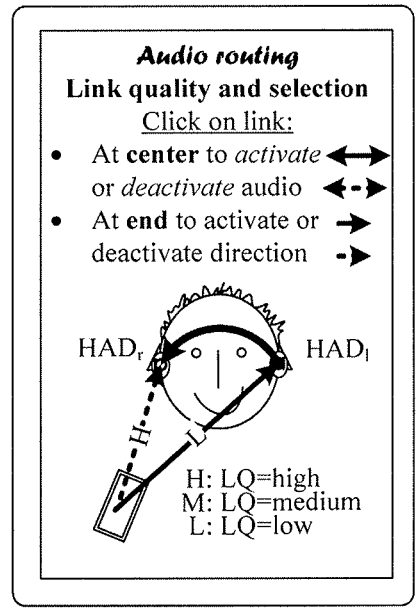
FIG. 7A  FIG. 7B
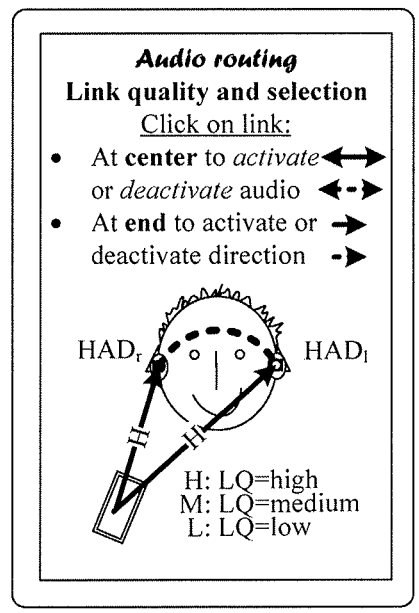
FIG. 7C

BINAURAL HEARING ASSISTANCE SYSTEM COMPRISING TWO WIRELESS INTERFACES

This application is a Continuation of copending application Ser. No. 14/534,282, filed on Nov. 6, 2014, which claims priority under 35 U.S.C. § 119(a) to Application No. 13191944.1, filed in Europe on Nov. 7, 2013, all of which are hereby expressly incorporated by reference into the present application.

TECHNICAL FIELD

The present application relates to wireless communication between portable communication devices, in particular applications involving a binaural hearing assistance system. The disclosure relates specifically to a binaural hearing assistance system comprising first and second hearing assistance devices adapted for being located at or in or fully or partially implanted in the head at left and right ears of a user.

The application furthermore relates to a method of operating a binaural hearing assistance system.

Embodiments of the disclosure may e.g. be useful in binaural hearing assistance systems, e.g. in a binaural hearing aid system, a pair of ear phones, a pair of active ear protection devices, etc.

BACKGROUND

The following account of the prior art relates to one of the areas of application of the present application, hearing aids.

Wireless links between mobile devices is of increasing importance. In connection with hearing aids, inductive links based on utilizing near-field properties of the electromagnetic field (inductive coupling between inductor coils in respective devices) communication have been widely used due to their relatively low power consumption (and appropriate, short range). The huge penetration of mobile telephones comprising wireless link capabilities based on far-field properties of the electromagnetic field (radiated fields, RF) and complying with the Bluetooth standard has influenced the field of hearing aids as well. Increasingly, wireless links involving hearing aids or accessories for hearing aids are based on Bluetooth or other proprietary or standardized, relatively low power (and correspondingly short range, e.g. less than 100 m) technologies (e.g. Bluetooth Low Energy, DECT, Wi-Fi (IEEE 802.11), ZigBee, etc.). In some cases, wireless links based on radiated fields and Bluetooth (operating in a non-licensed frequency range, e.g. ISM (ISM=Industrial, Scientific and Medical), e.g. around 865 MHz or 2.4 GHz) have replaced or taken the place of the inductive links.

When transmitting data on an RF carrier (e.g. in the GHz range) in a complex environment, the signal at the receiver will be impacted by two fading effects:
- attenuation due to lossy materials (e.g. a body).
- negative interference due to multipath effects (reflections from walls, etc., multi-path fading).

As the device comprising the RF-receiver moves around in the complex environment relative to the RF-transmitter, the severity of the fading may change dramatically.

An RF-transmission comprising audio to a hearing aid from an audio delivery device (e.g. an audio gateway, a cellphone, a TV, a microphone, or other accessory) will be subject to the above challenges. Hence, reception from transmitting devices that are not provided with advanced means for compensating such variable fading effects (such as diversity antennas) will be challenging. In such cases, the problems must be solved at the receiving end, e.g. in a hearing aid.

US2008159548A1 describes wireless stereo reception of first and second audio information by wireless hearing communication devices, e.g. hearing assistance devices, such as hearing aids. Various forms and protocols of signal transmission are employed in varying embodiments, including various communication modes such as eavesdropping modes and relaying modes.

US2007291970A1 deals with wireless communication between hearing units of small construction, especially between hearing aids with an increased data rate. A hearing unit is fitted with a transceiver which has an inductive receiving device and a digital wideband pulse transmitter. Two such hearing units can then communicate wirelessly with one another with the help of a communication station which is structurally separate from the hearing units and with which a message can be transmitted from the one to the other of the hearing units. The digital wideband pulse transmitter can be implemented in a structurally small manner in the hearing unit and with low power consumption.

SUMMARY

In the case where a user is equipped with a hearing assistance device on both ears (constituting a bilateral or binaural hearing aid system), it will be possible to utilize a (low frequency) near-field (NF), e.g. magnetic (inductive), ear-to-ear communication link to solve the fading challenge of (high frequency) communication links based on radiated fields (RF) (due to the RF-attenuating (diffracting) medium constituted by the human head (and body)).

An object of the present application is to provide an improved binaural hearing assistance system. In an embodiment, an object of the application is to provide an improved reliability of reception by the binaural hearing assistance system of an audio signal from an auxiliary device.

Objects of the application are achieved by the invention described in the accompanying claims and as described in the following.

A Hearing Assistance Device:

In an aspect of the present application, an object of the application is achieved by A binaural hearing assistance system comprising first and second hearing assistance devices adapted for being located at or in or fully or partially implanted in the head at left and right ears of a user wherein each of the first and second hearing assistance devices comprises
- a) a first wireless interface comprising first antenna and transceiver circuitry adapted for establishing a first communication link to the respective other hearing assistance device based on near-field communication;
- b) a second wireless interface comprising second antenna and transceiver circuitry adapted for establishing a second communication link to an auxiliary device based on far-field communication;
- c) a link control unit operatively coupled to the second antenna and transceiver circuitry and configured to repeatedly provide a second link quality measure indicative of a link quality of the second communication link;

wherein the first and second hearing assistance devices are configured to exchange said respective second link quality measures between them via said first and/or second communication links.

This has the advantage of providing a robust and flexible system. This is particularly valuable in systems, such as binaural hearing aid systems, where audio quality and power consumption has to be mutually optimized.

In an embodiment, the binaural hearing assistance system is configured to provide that control signals (e.g. including link quality measures LQ1 and/or LQ2 for the first and second communication links, respectively) can be exchanged between first and second hearing assistance devices via the first and/or second communication links. In an embodiment, the binaural hearing assistance system is configured to provide that audio signals (e.g. including full bandwidth audio signals or selected frequency bands, comprising frequencies in a range between a minimum and a maximum frequency, e.g. between 0 and 8 kHz) can be exchanged between the auxiliary device(s) and the first and second hearing assistance devices via the second communication links. In an embodiment, the binaural hearing assistance system is configured to provide that audio signals can be exchanged between the first and second hearing assistance devices via the first communication link. The term 'exchanged' is in the present context taken to include that data can be forwarded from one device to the other and vice versa (bi-directional transmission).

In an embodiment, the first and second hearing assistance devices are configured to communicate with the same auxiliary device via the second communication link. In an embodiment, the signals transmitted by the auxiliary device to the first and second hearing assistance devices are identical. In an embodiment, the signals transmitted by the auxiliary device to the first and second hearing assistance devices are different (e.g. comprising stereo audio signals). Alternatively, however, the first and second hearing assistance devices are adapted to communicate with different auxiliary devices via the second communication link.

In an embodiment, the link control unit is configured to control the first communication link dependent of the respective second link quality measures.

In an embodiment, the binaural hearing assistance system is configured to provide that the respective second link quality measures are exchanged between the first and second hearing assistance devices via the first and/or second communication links (at least) in an audio reception mode, where audio signals are to be received from the auxiliary device. Likewise, the binaural hearing assistance system is configured to provide that the first communication link is controlled dependent of the respective second link quality measures (at least) in said audio reception mode.

In an embodiment, the link control unit is operatively coupled to the first antenna and transceiver circuitry and configured to repeatedly provide a first link quality measure LQ1 indicative of a link quality of the first communication link, in particular regarding a quality of a signal received via the first communication link.

In an embodiment, the first and second hearing assistance devices are configured to exchange said respective first link quality measures between them via said first and/or second communication links.

In an embodiment, the first and second hearing assistance devices are configured to exchange said respective first and/or second link quality measures between them via said first communication link. In an embodiment, the first and second hearing assistance devices are configured to exchange said respective first and/or second link quality measures between them via said second communication link and said auxiliary device.

In an embodiment, each hearing assistance device is configured to control a transmission to the other hearing assistance device based on (or influenced by) a first link quality measure received from the other hearing assistance device.

In an embodiment, the first and/or second link quality measures comprise a signal strength or a bit error rate of a signal transmitted over said second links. In an embodiment, a measure of link quality (LQ) is e.g. based on the signal strength of the received signal (e.g. based on the RSSI (received signal strength indication), cf. IEEE 802.11 (WiFi)) and/or its bit error rate and/or the gain-settings of the receiver (e.g. of an automatic gain control (AGC) unit) of the receiving (or transmitting) device (forming part of the second wireless interface). In an embodiment, the measure of the quality of the link is based on the gain of an automatic gain control (AGC) unit necessary to achieve a predefined signal to noise ratio (S/N) or bit error rate (BER) of the received signal. In an embodiment, the measure of the quality of the link is additionally based on the field strength of the received signal. In an embodiment, the (time dependent) first and second link quality measures (LQ1 and LQ2) indicative of a link quality of the first and second communication links are updated with regular update frequencies $f_{upd1}$, $f_{upd2}$, respectively. In an embodiment, $f_{upd1}=f_{upd2}$. The update frequencies may alternatively be different or the update(s) may additionally or alternatively be provided on demand, e.g. via a user interface. In an embodiment, an update frequency is larger than 0.01 Hz, e.g. in the range from 0.1 Hz to 10 Hz. In an embodiment, link quality measures LQ1 and LQ2 comprise status indications of the first and second transceiver circuitry. In an embodiment, the binaural hearing assistance device is configured to forward information about a poor link quality measure (e.g. a received signal strength or a transceiver status) of a $2^{nd}$ communication link between the auxiliary device and one of the first or second hearing assistance devices to the auxiliary device via (a back-link comprising) the first communication link, the opposite hearing assistance device and the second communication link back to the auxiliary device. Thereby a status information of a malfunctioning link or transceiver circuitry can be conveyed to the auxiliary device and an appropriate action taken.

In an embodiment, the first communication link is an inductive link. An inductive link is e.g. based on mutual inductive coupling between respective inductor coils of the first and second hearing assistance devices. In an embodiment, the frequencies used to establish the first communication link between the first and hearing assistance devices are relatively low, e.g. below 100 MHz, e.g. located in a range from 1 MHz to 50 MHz, e.g. below 10 MHz. In an embodiment, the first communication link is based on a standardized or proprietary technology. In an embodiment, the first communication link is based on NFC or RuBee. In an embodiment, the first communication link is based on a proprietary protocol, e.g. as defined by US 2005/0255843 A1.

In an embodiment, the second communication link is based on radiated fields. In an embodiment, the second communication link is based on a standardized or proprietary technology. In an embodiment, the second communication link is based on Bluetooth technology (e.g. Bluetooth Low-Energy technology). In an embodiment, the communication protocol or standard of the second communication link is configurable, e.g. between a Bluetooth SIG Specification and one or more other standard or proprietary protocols (e.g. a modified version of Bluetooth, e.g. Bluetooth Low Energy modified to comprise an audio layer). In an embodiment, the first and second hearing assistance devices are adapted to establish the second communication link to an auxiliary device (e.g. to different auxiliary devices) according to different standardized or proprietary wireless communication technologies. In an embodiment, the communication protocol or standard of the second communication link of the first hearing assistance device is classic Bluetooth as specified by the Bluetooth Special Interest Group (SIG). In an embodiment, the communication protocol or standard of the second communication link of the second hearing assistance device is another standard or proprietary protocol (e.g. a modified version of Bluetooth, e.g. Bluetooth Low Energy modified to comprise an audio layer). Thereby, the first and second hearing assistance devices can receive signals (e.g. audio and/or data signals) from two different auxiliary devices, and relevant signals (e.g. audio and/or data (e.g. control) signals) can be exchanged between the two hearing assistance devices via the first communication link.

In an embodiment, the first and second hearing assistance devices are adapted to establish the second communication link to an auxiliary device according to different standardized or proprietary wireless communication technologies.

In an embodiment, the communication between the respective first and second hearing assistance devices and the auxiliary device is based on some sort of modulation at frequencies above 100 kHz. Preferably, frequencies used to establish the second communication link between the respective first and hearing assistance devices and the auxiliary device is below 70 GHz, e.g. located in a range from 50 MHz to 50 GHz, e.g. above 300 MHz, e.g. in an ISM range above 300 MHz, e.g. in the 900 MHz range or in the 2.4 GHz range or in the 5.8 GHz range or in the 60 GHz range (such standardized ranges being e.g. defined by the International Telecommunication Union, ITU).

In an embodiment, a center frequency of the frequency range of the second communication link is at least two times larger than a center frequency of the frequency range of the first communication link, such as at least 5 times larger, such as at least 10 times larger, such as at least 50 times larger, such as at least 100 times larger than a center frequency of the frequency range of the first communication link.

In an embodiment, threshold values $LQ1_{th}$ and/or $LQ2_{th}$ of the first and second link quality measures LQ1 and LQ2 are defined to separate a GOOD from a BAD link quality for the first and/or second communication links, respectively. In an embodiment, first threshold values $LQ1_{th}$ of the first link quality measure LQ1 are defined (and e.g. stored in the respective link control units of the first and second hearing assistance devices), the first threshold values $LQ1_{th}$ being determined to separate a GOOD from a BAD link quality for the first communication link. In an embodiment, second threshold values $LQ2_{th}$ of the second link quality measures LQ2 are defined (and e.g. stored in the respective link control units of the first and second hearing assistance devices), the second threshold values $LQ2_{th}$ being determined to separate a GOOD from a BAD link quality for the second communication links. In an embodiment, more than one threshold of the first and/or second link quality measures are defined to allow a more gradual valuation of the link quality measure in question (e.g. comprising three different levels, e.g. denoted GOOD, MEDIUM, BAD).

In an embodiment, the binaural hearing assistance system is configured to receive an audio signal in one of said first and second hearing assistance devices ($HAD_1$, $HAD_2$) from an auxiliary device via said second communication link and to relay it via said first communication link to the other hearing assistance device, in case the link quality measures as determined in said first and second hearing assistance devices fulfil a predefined criterion.

In an embodiment, the predefined criterion comprises that a difference in said second link quality measures as determined in said first and second hearing assistance devices is above a predetermined minimum value and/or if said second link quality measure regarding one of the second communication links is below a predefined threshold value.

If e.g., during streaming of an audio signal from an auxiliary (audio delivery) device over the second (RF–) communication link to the first and second hearing assistance devices ($HAD_1$, $HAD_2$), the first hearing assistance device ($HAD_1$) experiences a poor signal or link quality on the second (RF–) communication link (if e.g. $LQ2(HAD_1)<LQ2_{th}$, indicating a BAD link quality), the link control unit of the second hearing assistance device ($HAD_2$) is configured to relay the audio signal received from the audio delivery device via the second communication link to the first hearing assistance device ($HAD_1$) via the first (e.g. magnetic) communication link. If, on the other hand, the first hearing assistance device ($HAD_1$) experiences a signal of better quality than the second hearing assistance device ($HAD_2$) (if e.g. $LQ2(HAD_1)-LQ2(HAD_2)>\Delta LQ2$, where $\Delta LQ2$ is a minimum predefined quality difference), the fading challenge can be resolved by relaying the audio signal received from the audio delivery device by the first hearing assistance device ($HAD_1$) to the second hearing assistance device ($HAD_2$) via the first (e.g. magnetic) link.

Preferably, the first and second hearing assistance devices ($HAD_1$, $HAD_2$) are configured to continuously monitor the quality of the received signal via the second (RF–) communication link and exchange information about the measured quality over the first (magnetic) communication link in order to ensure that the first (magnetic) communication link is (only) activated (set up), when needed (and possibly deactivated, when not, to save power). Thereby it can be achieved that the best possible audio signal quality will always be provided to the hearing assistance devices, even in case of a poor quality of an audio signal received from one of the second (RF–) communication links.

In an embodiment, the 're-routing' (or relay) via the first communication link of an audio signal received from an audio delivery device via the second communication link will only be established in case the quality of the second (RF–) communication link drops below a certain threshold (if e.g. $LQ2(HAD_1)-LQ2(HAD_2)>\Delta LQ2$, and/or if $LQ2(HAD_i)<LQ2_{th}$, i=1 or 2). Thereby power can be saved and/or system complexity minimized.

In an embodiment, the quality of the second (and/or the first) communication link is monitored over time (e.g. by storing values of a link quality measure at different points in time in a memory of the binaural hearing assistance system, e.g. in the hearing assistance device(s)). Thereby, a need for maintenance and/or a change of operational parameters of components of the communication links can be predicted.

Typically, the hearing assistance devices are portable devices comprising a local energy source, e.g. a battery, e.g. a rechargeable battery. Portable hearing assistance devices are in general small devices (e.g. ≤0.05 m) that work under power constraints (where battery life time or the time between recharging is limited to hours or days). In addition to improving the overall quality of the audio signals received by the binaural hearing assistance system, an improved utilization of the local energy source can be provided by the present disclosure. The fraction of the power consumption of a binaural hearing assistance system attributable to the wireless link(s) can be substantial. Hence, it is of interest to minimize power consumed by the wireless link(s) to improve battery life time. Typically, the first communication link has a lower power consumption than the second communication link. Typically, reception in the first communication link has a lower power consumption than reception in the second communication link.

In an embodiment, each of the hearing assistance devices comprise an energy source status monitoring circuit configured to monitor the current status of the local energy source and to provide a corresponding energy status indication signal, and to exchange said energy status indication signal with the other hearing assistance device of the binaural hearing assistance system via the first and/or the second communication link.

In an embodiment, each of the hearing assistance devices comprise an energy source (e.g. a battery) status monitoring circuit configured to monitor the current status of the local energy source (e.g. one or more of its voltage, maximum current, temperature) and provide an energy status indication signal (e.g. indicative of a rest capacity of the energy source, e.g. an estimated time before exchange or recharge is necessary). In an embodiment, the energy status signals are repeatedly provided, to avail a current status of the energy source (e.g. a battery) in the hearing assistance devices. In an embodiment, the energy source status monitoring circuit is operatively coupled to the link control unit.

In an embodiment, the link control unit of each of the hearing assistance devices is configured to exchange the energy status signals between them (so that each hearing assistance device has access to its own status and the status of the opposite hearing assistance device) via said first and/or second communication links. In an embodiment, the energy status indication signals are exchanged via the first communication link.

In an embodiment, at least one of the hearing assistance devices (e.g. both, e.g. a link control unit of at least one of the hearing assistance devices) is configured to control the first and/or second communication link dependent on the respective energy status indication signal(s) (e.g. dependent of one of or both energy status indication signals).

In an embodiment, the binaural hearing assistance system is configured—in a specific power saving mode of operation where the energy status indication signal in the first hearing assistance device fulfils a predefined low status criterion—to relay an audio signal received from the auxiliary device by the second hearing assistance device to the first hearing assistance device via the first communication link.

The audio signal (possibly comprising additional control, status or other information, e.g. embedded therein) is received from the or an auxiliary device via the second communication link(s). In the power saving mode, the second communication link of the first hearing assistance device can be brought into a low power mode (to thereby lower drain on the energy source). The hearing assistance device for which the energy status indication signal fulfils the predefined 'low status criterion' can of course be any of the first and second hearing assistance devices. In an embodiment, the predefined low status criterion comprises that the energy status indication signal ES is below a threshold value $ES_{th}$. In an embodiment, the predefined low status criterion comprises that the (numerical) difference ($|ES_1-ES_2|$) between energy status indication signals ES of the first and second hearing assistance devices is above a predefined difference value AES.

In an embodiment, the binaural hearing assistance system is configured—in a specific power saving mode of operation—to only receive an audio signal from the auxiliary device in one of the hearing assistance devices and relay the received audio signal to the other hearing assistance device via the first communication link. In an embodiment, the binaural hearing assistance system is configured—in the specific power saving mode of operation—to alternatingly select the hearing assistance device that receives the audio signal from the auxiliary device and relays it to the other hearing assistance device via the first communication link as the first and second hearing assistance device, respectively (so that only one of the second communications links between an auxiliary device and a hearing assistance device is actively receiving audio (or is active at all) at a given time, cf. FIG. 6). In an embodiment, the binaural hearing assistance system is configured to switch between the first and second hearing assistance device chosen to receive audio signals from the auxiliary device every time the system is powered up after a power down. Alternatively, the binaural hearing assistance system is configured to switch between the first and second hearing assistance device (as the sole recipient of an audio signal via the second communication link) with a predefined switch frequency, e.g. every hour, and/or controlled by a user via a user interface.

Preferably, the link control unit is configured to give a different priority to the link quality measures than to the energy status indication signal during control of the first and/or second communication links (to ensure that a (possibly sole) high quality second communication link is NOT powered down due to power consumption considerations.

In an embodiment, the first antenna and transceiver circuitry of the first and second hearing assistance devices comprises an inductive antenna, e.g. an inductor coil. Alternatively, a capacitive antenna may be used. In an embodiment, the second antenna and transceiver circuitry of the first and second hearing assistance devices comprises an antenna adapted to radiate electromagnetic fields, e.g. a Bluetooth antenna, e.g. a dipole, a patch or a loop antenna.

In an embodiment, the binaural hearing assistance system is configured to determine a first transfer function H1 between the first antenna and transceiver circuitry of the first hearing assistance device and the first antenna and transceiver circuitry of the second hearing assistance device and/or a second transfer function H2 between the second antenna and transceiver circuitry of the first hearing assistance device and the second antenna and transceiver circuitry of the second hearing assistance device.

A transfer function between the inductive antennas of the first and second hearing assistance devices will be different from a transfer function between the Bluetooth antennas of the first and second hearing assistance devices (e.g. depending on the transmission frequency ranges of the first and second communication links and the distance between and the diffractive media located between the first and second hearing assistance devices).

The transfer function for transmission between the inductive antennas mainly depend on the distance between the antennas, while the transfer function for transmission between the Bluetooth antennas will be affected by the energy loss in the medium between the antennas (e.g. a head, when the first and second hearing assistance devices are operationally mounted on the head of a user).

By transferring the transmission power from the transmitting device to the receiving device, the transfer function between the two antennas can be estimated at the receiving device. In an embodiment, the binaural hearing assistance system is configured to transfer a transmission power ($P_{Tx,i}$, i=1, 2) of the first and/or second antenna and transceiver circuitry of the first hearing assistance device to the second hearing assistance device, (and in the second hearing assistance device) to extract corresponding received power ($P_{Rx,i}$, i=1, 2) or the first and/or second communication links, respectively, and to estimate said first and/or second transfer functions H1 and/or H2, respectively, from said respective transferred transmission and received powers. In an embodiment, the individual transfer functions Hi, i=1, 2, are estimated as $P_{Rx,i}/P_{Tx,i}$, i=1, 2. In an embodiment, the transfer functions from the second to the first hearing assistance device may be estimated (in the first hearing assistance device) by a corresponding procedure.

In an embodiment, the binaural hearing assistance system is configured to decide whether or not the first and second hearing assistance devices are operationally mounted on the head of the user based on said first and second transfer functions.

Knowledge about the transfer functions between the two of antennas of each set of antennas of the hearing assistance devices when mounted at each ear of a user (and their current values) may be used to detect whether or not the hearing assistance devices are operationally mounted at each ear of the user. By combining (e.g. comparing) the estimated transfer functions for the two different types of wireless interfaces (inductive and Bluetooth), the detection accuracy can be improved (e.g. by further consideration of other parameters, e.g. a movement sensor). In an embodiment, the binaural hearing assistance system is configured to estimate the first and second transfer functions (H1, H2) at predetermined time instances, e.g. with a regular frequency (e.g. less than 0.01 Hz) or initiated by a predefined criterion regarding the first and second link quality measures and/or other measures, e.g. provided by other detectors/sensors. In an embodiment, the binaural hearing assistance system is configured to enter a power down mode, when said current values of said first and second transfer functions fulfill a predefined criterion (e.g. if said first and second transfer functions are both larger than a typical value of the respective transfer functions when operatively mounted on the user's head), and/or if said second transfer function is much larger than a typical value. In an embodiment, the current values of the first and/or second transfer functions is/are used (possibly together with other indicators) as inputs to a control unit for deciding whether or not the hearing assistance system (or one or both of the hearing assistance devices) should enter another mode of operation, e.g. low power mode, a power down mode, a power up mode, etc. A hearing assistance device with a low power mode that is entered or not in dependence of a multitude of sensor inputs is e.g. described in our co-pending US patent application having application Ser. No. 13/869,661, filed on 24 Apr. 2013.

In an embodiment, the communication via the wireless link is arranged according to a specific modulation scheme, e.g. an analogue modulation scheme, such as FM (frequency modulation) or AM (amplitude modulation) or PM (phase modulation), or a digital modulation scheme, such as ASK (amplitude shift keying), e.g. On-Off keying, FSK (frequency shift keying), PSK (phase shift keying) or QAM (quadrature amplitude modulation).

In an embodiment, the hearing assistance device and/or the communication device comprises an electrically small antenna. An 'electrically small antenna' is in the present context taken to mean that the spatial extension of the antenna (e.g. the maximum physical dimension in any direction) is much smaller than the wavelength $\lambda_{Tx}$ of the transmitted electric signal. In an embodiment, the term much smaller is taken to mean more than 3 times, such as more than 10 times smaller, such as more than 20 times small than the operating wavelength of a wireless interface to which the antenna is intended (ideally an antenna for radiation of electromagnetic waves at a given frequency should be larger than or equal to half the wavelength of the radiated waves at that frequency). At 860 MHz, the wavelength in vacuum is around 35 cm. At 2.4 GHz, the wavelength in vacuum is around 12 cm. In an embodiment, the hearing assistance device has a maximum outer dimension of the order of 0.15 m (e.g. a handheld mobile telephone). In an embodiment, the hearing assistance device has a maximum outer dimension of the order of 0.08 m (e.g. a head set). In an embodiment, the hearing assistance device has a maximum outer dimension of the order of 0.04 m (e.g. a hearing instrument).

In an embodiment, the hearing assistance device is portable device, e.g. a device comprising a local energy source, e.g. a battery, e.g. a rechargeable battery.

In an embodiment, the hearing assistance device comprises a forward or signal path between an input transducer (microphone system and/or direct electric input (e.g. a wireless receiver)) and an output transducer. In an embodiment, a signal processing unit is located in the forward path. In an embodiment, the signal processing unit is adapted to provide a frequency dependent gain according to a user's particular needs. In an embodiment, the hearing assistance device comprises an analysis path comprising functional components for analyzing the input signal (e.g. determining a level, a modulation, a type of signal, an acoustic feedback estimate, a link quality measure, a signal quality measure, etc.). In an embodiment, some or all signal processing of the analysis path and/or the signal path is conducted in the frequency domain. In an embodiment, some or all signal processing of the analysis path and/or the signal path is conducted in the time domain.

In an embodiment, the hearing assistance devices comprise an analogue-to-digital (AD) converter to digitize an analogue input with a predefined sampling rate, e.g. 20 kHz. In an embodiment, the hearing assistance devices comprise a digital-to-analogue (DA) converter to convert a digital signal to an analogue output signal, e.g. for being presented to a user via an output transducer.

In an embodiment, each hearing assistance device comprise(s) a TF-conversion unit for providing a time-frequency representation of an input signal. In an embodiment, the time-frequency representation comprises an array or map of corresponding complex or real values of the signal in question in a particular time and frequency range. In an embodiment, the TF conversion unit comprises a filter bank for filtering a (time varying) input signal and providing a number of (time varying) output signals each comprising a distinct frequency range of the input signal. In an embodiment, the TF conversion unit comprises a Fourier transformation unit (e.g. based on a DFT-, e.g. an FFT-algorithm) for converting a time variant input signal to a (time variant) signal in the frequency domain.

In an embodiment, the hearing assistance device comprises a level detector (LD) for determining the level of an input signal (e.g. on a band level and/or of the full (wide band) signal).

In a particular embodiment, the hearing assistance device comprises a voice detector (VD) for determining whether or not an input signal comprises a voice signal (at a given point in time).

In an embodiment, the hearing assistance device further comprises other relevant functionality for the application in question, e.g. compression, noise reduction, feedback cancellation, etc.

In an embodiment, the hearing assistance device comprises a listening device, e.g. a hearing aid, e.g. a hearing instrument, e.g. a hearing instrument adapted for being located at the ear or fully or partially in the ear canal of a user, e.g. a headset, an earphone, an ear protection device or a combination thereof.

In an embodiment, the binaural hearing assistance system comprises the auxiliary device.

In an embodiment, the binaural hearing assistance system is adapted to establish the first communication link between the first and second hearing assistance devices and second communication links between each of the first and second hearing assistance devices and the auxiliary device to provide that information (e.g. control and status signals (e.g. link quality measures), and audio signals) can be exchanged between or forwarded from one to the other.

In an embodiment, the binaural hearing assistance system comprises a user interface (e.g. a remote control, e.g. implemented as an APP of a SmartPhone) from which a user can select a suitable routing of an audio signal from the auxiliary device to each of the first and second hearing assistance devices, e.g. by activating or deactivating a link in the current arrangement of devices (e.g. via a graphical interface illustrating current audio links and their link quality).

In an embodiment, the auxiliary device is or comprises an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing assistance device. In an embodiment, the auxiliary device is or comprises a remote control for controlling functionality and operation of the hearing assistance device(s). In an embodiment, the auxiliary device is or comprises a cell phone, e.g. a SmartPhone. In an embodiment, the hearing assistance device(s) comprises an appropriate wireless interface to the SmartPhone, e.g. based on Bluetooth or some other standardized or proprietary scheme, e.g. based on radiated electromagnetic fields.

In the present context, a SmartPhone, may comprise
a (A) cellular telephone comprising a microphone, a speaker, and a (wireless) interface to the public switched telephone network (PSTN) COMBINED with
a (B) personal computer comprising a processor, a memory, an operative system (OS), a user interface (e.g. a keyboard and display, e.g. integrated in a touch sensitive display) and a wireless data interface (including a Web-browser), allowing a user to download and execute application programs (APPs) implementing specific functional features (e.g. displaying information retrieved from the Internet, remotely controlling another device, combining information from various sensors of the SmartPhone (e.g. camera, scanner, GPS, microphone, etc.) and/or external sensors to provide special features, etc.).

In an embodiment, the auxiliary device is or comprises another hearing assistance device, e.g. one of the first and second hearing assistance devices. In an embodiment, the first and second hearing assistance devices are configured to (e.g. in a specific mode of operation) to establish the second communicate link between them.

Use:

In an aspect, use of a hearing assistance device as described above, in the 'detailed description of embodiments' and in the claims, is moreover provided. In an embodiment, use is provided in a system comprising audio distribution, e.g. a system comprising a microphone and a loudspeaker in sufficiently close proximity of each other to cause feedback from the loudspeaker to the microphone during operation by a user. In an embodiment, use is provided in a system comprising one or more hearing instruments, headsets, ear phones, active ear protection systems, etc., e.g. in handsfree telephone systems, teleconferencing systems, public address systems, karaoke systems, classroom amplification systems, etc.

A Method:

In an aspect, A method of operating a binaural hearing assistance system comprising first and second hearing assistance devices adapted for being located at or in or fully or partially implanted in left and right ear regions of a user is furthermore provided by the present application. The method comprises in each of the first and second hearing assistance devices
  a) providing a first wireless interface adapted for establishing a first communication link to the respective other hearing assistance device based on near-field communication;
  b) providing a second wireless interface adapted for establishing a second communication link to an auxiliary device based on far-field communication;
  c) repeatedly providing a second link quality measure indicative of a link quality of the second communication link; and exchanging said respective second link quality measures between the first and second hearing assistance devices via said first and/or second communication links.

It is intended that some or all of the structural features of the device described above, in the 'detailed description of embodiments' or in the claims can be combined with embodiments of the method, when appropriately substituted by a corresponding process and vice versa. Embodiments of the method have the same advantages as the corresponding devices.

A Computer Readable Medium:

In an aspect, a tangible computer-readable medium storing a computer program comprising program code means for causing a data processing system to perform at least some (such as a majority or all) of the steps of the method described above, in the 'detailed description of embodiments' and in the claims, when said computer program is executed on the data processing system is furthermore provided by the present application. In addition to being stored on a tangible medium such as diskettes, CD-ROM-, DVD-, or hard disk media, or any other machine readable medium, and used when read directly from such tangible media, the computer program can also be transmitted via a transmission medium such as a wired or wireless link or a network, e.g. the Internet, and loaded into a data processing system for being executed at a location different from that of the tangible medium.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

Definitions:

In the present context, a 'hearing assistance device' refers to a device, such as e.g. a hearing instrument or an active ear-protection device or other audio processing device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears. A 'hearing assistance device' further refers to a device such as an earphone or a headset adapted to receive audio signals electronically, possibly modifying the audio signals and providing the possibly modified audio signals as audible signals to at least one of the user's ears. Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing assistance device may be configured to be worn in any known way, e.g. as a unit arranged behind the ear with a tube leading radiated acoustic signals into the ear canal or with a loudspeaker arranged close to or in the ear canal, as a unit entirely or partly arranged in the pinna and/or in the ear canal, as a unit attached to a fixture implanted into the skull bone, as an entirely or partly implanted unit, etc. The hearing assistance device may comprise a single unit or several units communicating electronically with each other.

More generally, a hearing assistance device comprises an input transducer for receiving an acoustic signal from a user's surroundings and providing a corresponding input audio signal and/or a receiver for electronically (i.e. wired or wirelessly) receiving an input audio signal, a signal processing circuit for processing the input audio signal and an output means for providing an audible signal to the user in dependence on the processed audio signal. In some hearing assistance devices, an amplifier may constitute the signal processing circuit. In some hearing assistance devices, the output means may comprise an output transducer, such as e.g. a loudspeaker for providing an air-borne acoustic signal or a vibrator for providing a structure-borne or liquid-borne acoustic signal. In some hearing assistance devices, the output means may comprise one or more output electrodes for providing electric signals.

In some hearing assistance devices, the vibrator may be adapted to provide a structure-borne acoustic signal transcutaneously or percutaneously to the skull bone. In some hearing assistance devices, the vibrator may be implanted in the middle ear and/or in the inner ear. In some hearing assistance devices, the vibrator may be adapted to provide a structure-borne acoustic signal to a middle-ear bone and/or to the cochlea. In some hearing assistance devices, the vibrator may be adapted to provide a liquid-borne acoustic signal to the cochlear liquid, e.g. through the oval window. In some hearing assistance devices, the output electrodes may be implanted in the cochlea or on the inside of the skull bone and may be adapted to provide the electric signals to the hair cells of the cochlea, to one or more hearing nerves, to the auditory cortex and/or to other parts of the cerebral cortex.

A 'listening system' refers to a system comprising one or two hearing assistance devices, and a 'binaural listening system' refers to a system comprising one or two hearing assistance devices and being adapted to cooperatively provide audible signals to both of the user's ears. Listening systems or binaural listening systems may further comprise 'auxiliary devices', which communicate with the hearing assistance devices and affect and/or benefit from the function of the hearing assistance devices. Auxiliary devices may be e.g. remote controls, audio gateway devices, mobile phones, public-address systems, car audio systems or music players. Hearing assistance devices, listening systems or binaural listening systems may e.g. be used for compensating for a hearing-impaired person's loss of hearing capability, augmenting or protecting a normal-hearing person's hearing capability and/or conveying electronic audio signals to a person.

Further objects of the application are achieved by the embodiments defined in the dependent claims and in the detailed description of the invention.

As used herein, the singular forms "a," "an," and "the" are intended to include the plural foam as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof It will also be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The disclosure will be explained more fully below in connection with a preferred embodiment and with reference to the drawings in which:

FIGS. 7A-7C show embodiments of an auxiliary device functioning as a user interface for a binaural hearing aid system according the present disclosure, FIGS. 7A, 7B and 7C illustrating three different audio routing scenarios between the auxiliary device and the hearing assistance devices, such routing being selectable via the graphical user interface of the auxiliary device (e.g. based on link quality measures illustrated in the display).

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

Figure 1A:
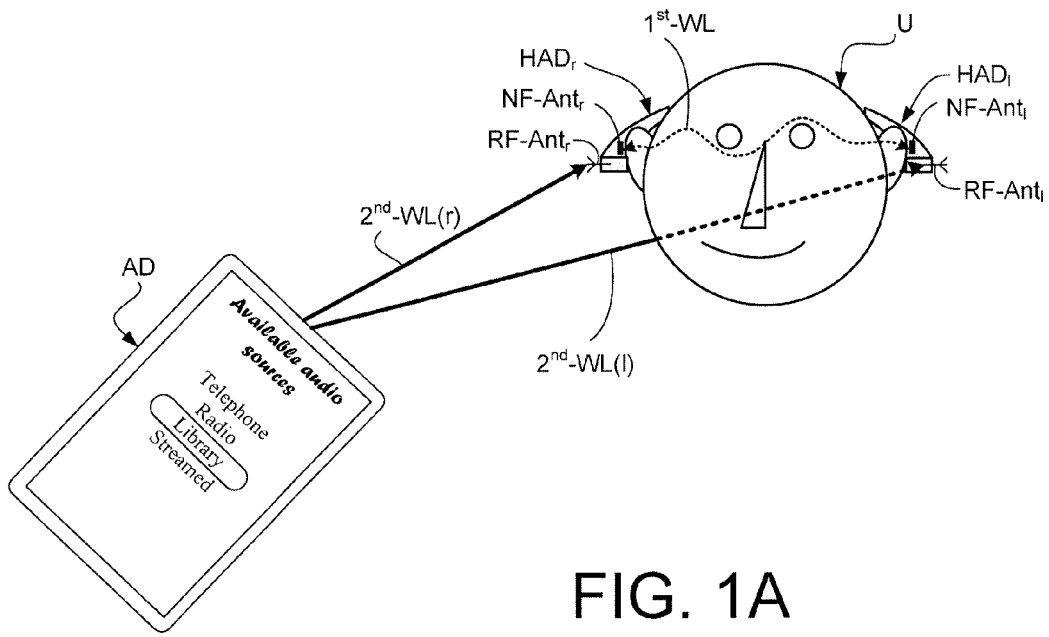
FIGS. 1A-1B show two application scenarios of a binaural hearing assistance system, FIG. 1A illustrating the two hearing assistance devices receiving an audio signal from an auxiliary (audio delivery) device via a wireless link, FIG. 1B illustrating a situation where audio signals from two different audio sources (a TV and a microphone, respectively) are wirelessly transmitted to and available for reception in the two hearing assistance devices.
Figure 1B:
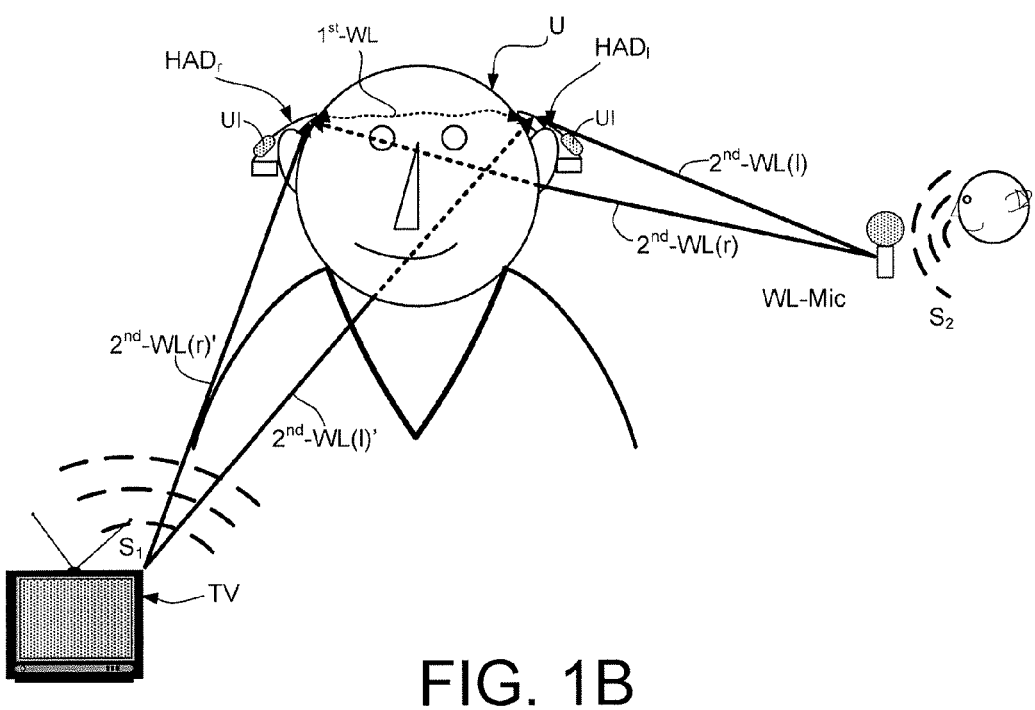

FIGS. 1A-1B show two application scenarios of a binaural hearing assistance system. In FIGS. 1A-1B, each of the left and right hearing assistance devices are adapted for being located at and/or in left and right ears of a user U and comprises a first wireless interface comprising first antenna (NF-ANT) and transceiver circuitry adapted for establishing a first communication link ($1^{st}$-WL) to the respective other hearing assistance device based on near-field communication (e.g. magnetic/inductive), and a second wireless interface comprising second antenna (RF-Ant) and transceiver circuitry adapted for establishing a second communication link ($2^{nd}$-WL) to an auxiliary device (AD) based on far-field communication (radiated fields, RF). Each of the left and right hearing assistance devices ($HAD_l$, $HAD_r$) further comprises a link control unit operatively coupled to the second antenna (RF-Ant) and transceiver circuitry and configured to repeatedly provide a second link quality measure indicative of a link quality of the second communication link ($2^{nd}$-WL). The left and right hearing assistance devices ($HAD_l$, $HAD_r$) are each configured to exchange the respective second link quality measures between them via said first and/or second communication links ($1^{st}$-WL, $2^{nd}$-WL(l), $2^{nd}$-WL(r)), preferably via said first communication link ($1^{st}$-WL).

If, e.g., during streaming from the audio delivery device (AD), e.g. embodied in a SmartPhone, over the RE-link ($2^{nd}$-WL(l), $2^{nd}$-WL(r)) to both hearing assistance devices ($HAD_l$, $HAD_r$), one of them, e.g. the left $HAD_l$, experiences a poor signal quality on the RF link ($2^{nd}$-WL(l) in FIG. 1A), e.g. due to attenuation of the RF-signal by a diffractive medium (e.g. the head of the user, as indicated by the dashed line part of the propagation path of the link ($2^{nd}$-WL(l)), it will be possible to use the magnetic link ($1^{st}$-WL) to receive a relayed audio stream from the right hearing assistance device $HAD_r$ (assumed to have a better signal quality). This situation is e.g. illustrated in FIG. 1A (AD=SmartPhone) and in FIG. 1B (AD=TV). If, on the other hand, the left hearing assistance device $HAD_l$ has a signal of better quality than $HAD_r$ (as e.g. illustrated by transmission of source $S_2$ from WL-Mic in FIG. 1B), the fading challenge can be solved by converting the RF stream of the left hearing assistance device $HAD_l$ to the magnetic link ($1^{st}$-WL) and relaying it to the right hearing assistance device $HAD_r$.

Preferably, both hearing assistance devices are configured to continuously monitor the quality of the RF signal received by the respective device, and to exchange information on this over the magnetic link ($1^{st}$-WL) in order to ensure that the magnetic link relay is set up when needed and is always transmitted to the hearing assistance device with the poorest quality RF link. Preferably, to save power and minimize complexity, the relay of audio signals will only be established in case the RF link quality of one of the RF-links drops below a certain threshold.

In a further embodiment, the binaural hearing assistance system is configured to monitor RF link quality over time (e.g. by regularly storing historic values of the link quality measure, and/or determining a running average) in order to enable a prediction of when the quality of the RF link to one of the hearing assistance devices will drop below an acceptable level.

FIG. 1A specifically illustrates the two hearing assistance devices ($HAD_l$, $HAD_r$) of the binaural hearing assistance system receiving the same audio signal from one auxiliary (audio delivery) device (AD) via respective (second) wireless RF-links ($2^{nd}$-WL(l), $2^{nd}$-WL(r)). In the scenario of FIG. 1A, the auxiliary device AD is shown to comprise a display showing a user currently available audio sources, and highlighting a selected one (here audio, e.g. music, from a Library of audio files, e.g. stored in a storage unit of the auxiliary device). The auxiliary device may thus comprise a user interface of the binaural hearing assistance system allowing a user to select a currently active audio source to be transmitted to the left and right hearing assistance devices. In an embodiment, auxiliary device AD is or forms part of a SmartPhone. In an embodiment, the RF link is based on Bluetooth, e.g. including Bluetooth Low energy. In an embodiment, the user interface may be configured to illustrate—and possibly allow a user to select (route)— which of the available links ($1^{st}$-WL, $2^{nd}$-WL(l), $2^{nd}$-WL(r)) to use for a given audio source at a given point in time. This feature (possibly implemented as an APP on a SmartPhone) is further discussed in connection with FIGS. 7A-7C.

FIG. 1B specifically illustrates a situation where audio signals from two different audio sources (a TV ($S_1$) and a wireless microphone ($S_2$), respectively) are wirelessly transmitted to and available for reception in the two hearing assistance devices ($HAD_l$, $HAD_r$) of the binaural hearing assistance system. In the scenario of FIG. 1B, two hearing assistance devices are shown each comprise a user interface UI allowing a user to influence the function of the hearing assistance system, e.g. to choose to listen to one particular of the currently received audio sources, or, alternatively, to select to listen to both of the currently received audio sources. In the embodiment of FIG. 1B, each hearing assistance device comprises a single (second) wireless RF-interface allowing each hearing assistance device to receive one audio signal at a time from a single of the currently available wireless RF-communication links. In an embodiment, each hearing assistance device comprises several (e.g. two, second, e.g. equal or different) wireless RF-interfaces allowing each hearing assistance device to receive two audio signals at a time from two of the currently available wireless RF-communication links. In the example of FIG. 1B, the RF-links from the wireless microphone (WL-Mic) is a standard Bluetooth link comprising separate links ($2^{nd}$-WL (l), $2^{nd}$-WL(r)) to the left and right hearing assistance devices (HAD$_l$, HAD$_r$), respectively, whereas the RF-links from the television set (TV) is a proprietary link (e.g. based on Bluetooth) comprising separate links ($2^{nd}$-WL(l)', $2^{nd}$-WL(r)') to the left and right hearing assistance devices, respectively. In an embodiment, the left and/or right hearing assistance devices comprise an input transducer (e.g. a microphone system) for converting acoustic sounds from the environment to electric input signals. In an embodiment, the hearing assistance devices comprise a selector and mixing unit connected to an output transducer allowing a specific or a (e.g. weighted) mixture of (some or all of) the available audio signals to be presented to the user as a perceivable sound.

In an alternative embodiment (not shown in FIG. 1B, but further discussed in connection with FIG. 5C), each hearing assistance device comprises a single wireless RF-interfaces allowing each hearing assistance device to receive one audio signal at a time from the currently available wireless RF-communication links, but each hearing assistance device comprises a wireless RF-interface that is different from the other (e.g. one is an interface according to the Bluetooth SIG-specification, and the other is a proprietary interface).

Figure 2:
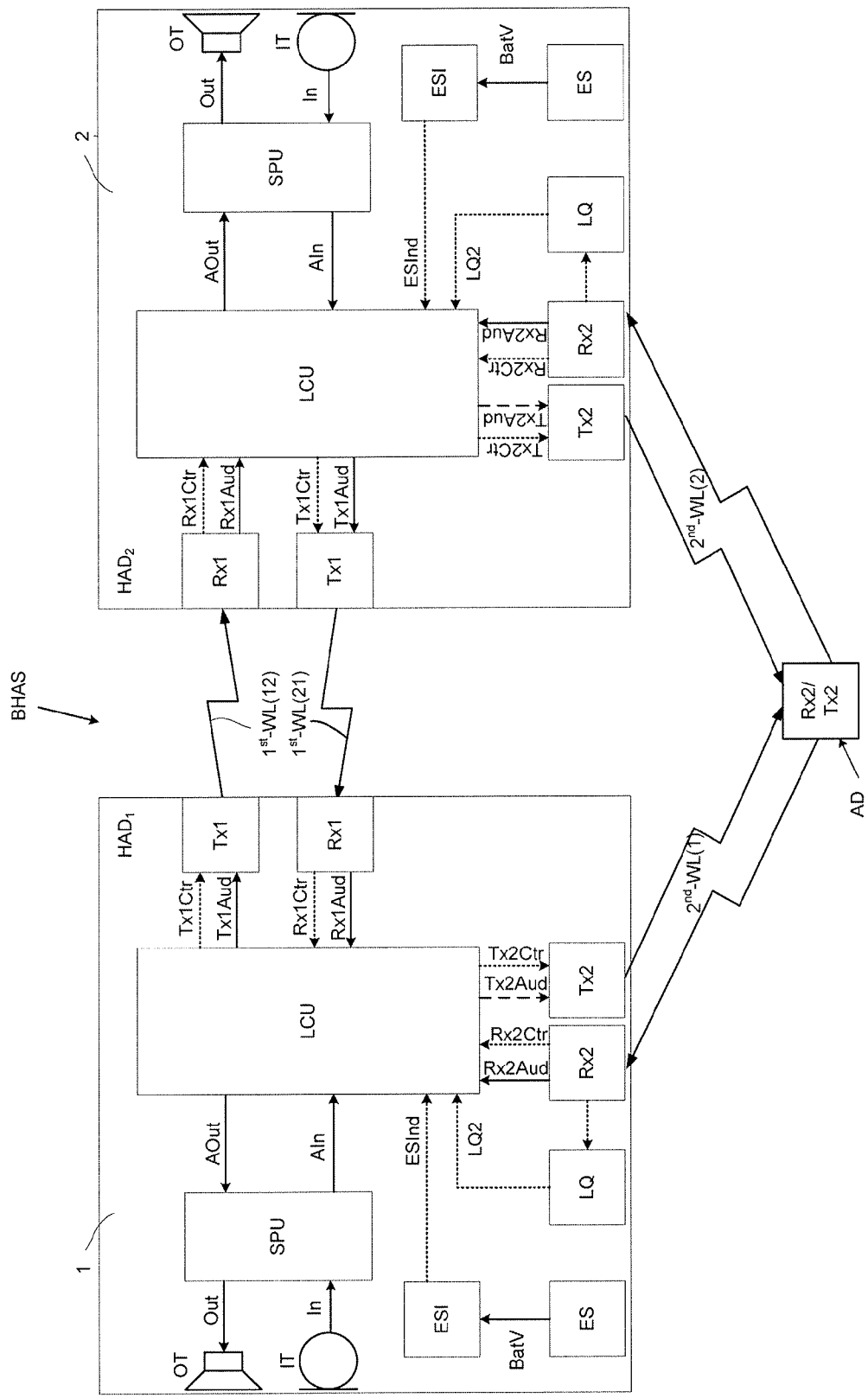
FIG. 2 shows an embodiment of a binaural hearing assistance system according to the present disclosure comprising first and second hearing assistance devices and an auxiliary device, the system being adapted for establishing wireless communication links between the devices.

FIG. 2 shows an embodiment of a binaural hearing assistance system BHAS according to the present disclosure comprising first and second hearing assistance devices (HAD$_1$, HAD$_2$) and an auxiliary device (AD), the system being adapted for establishing wireless communication links between the devices:

A bi-directional (first, inductive) link (1st-WL(12), 1st-WL(12)) between the first and second hearing assistance devices (HAD1, HAD2).

A bi-directional (second, RF) link (2nd-WL(1)) between the auxiliary device (AD) and the first hearing assistance device (HAD1).

A bi-directional (second, RF) link (2nd-WL(2)) between the auxiliary device (AD) and the first hearing assistance device (HAD$_2$).

The bi-directional (first, inductive) link ($1^{st}$-WL(12), $1^{st}$-WL(12)) is implemented by a first wireless interface comprising first antenna and transceiver circuitry (Rx1, Tx1) in the first hearing assistance device (HAD$_1$) as well as in the second hearing assistance device (HAD$_2$). The bi-directional (first, inductive) link may establish a uni-directional connection ($1^{st}$-WL(12) for transmission of audio (Tx1Aud) signals and/or control (Tx1Ctr) signals (e.g. including link quality measures) from the first (HAW hearing assistance device and received as corresponding audio (Rx1Aud) signals and control (Rx1Ctr) signals, respectively, in the second hearing assistance device (HAD$_2$). Likewise, The bi-directional (first, inductive) link may establish a uni-directional connection ($1^{st}$-WL(21) for transmission of audio (Tx1Aud) signals and/or control (Tx1Ctr) signals (e.g. including link quality measures) from the second (HAD$_2$) hearing assistance device and received as corresponding audio (Rx1Aud) signals and control (Rx1Ctr) signals, respectively, in the first hearing assistance device (HAD$_1$).

The two bi-directional (second, RF) links ($2^{nd}$-WL(1), $2^{nd}$-WL(2)) are implemented by second wireless interfaces comprising second antenna and transceiver circuitry (Rx2, Tx2) in the first hearing assistance device (HAD$_1$) as well as in the second hearing assistance device (HAD$_2$) and antenna and transceiver circuitry (Rx2/Tx2) in the auxiliary device.

The bi-directional (second, RF) link ($2^{nd}$-WL(1)) between the first hearing assistance device (HAD.) and the auxiliary device (AD) may be configured to transmit control (Tx2Ctr) signals (e.g. including link quality measures) and optionally audio (Tx2Aud, indicated in dashed line) signals from the first (HAD$_1$) hearing assistance device and received as corresponding audio and control signals, respectively, in the auxiliary device (AD) and correspondingly to receive in the first (HAD$_1$) hearing assistance device audio (Rx2Aud) signals and/or control (Rx2Ctr) signals from the auxiliary device (AD). The bi-directional (second, RF) link ($2^{nd}$-WL (2)) between the second hearing assistance device (HAD$_2$) and the auxiliary device (AD) may be correspondingly configured.

In each of the embodiments of first and second hearing assistance devices shown in FIG. 2, a link control unit LCU is operatively connected to (transceiver circuitry of) the first and second wireless interfaces via the transmitted and received audio and control signals (Tx1Aud, Tx1Ctr, Rx1Aud, Rx1Ctr) and (Tx2Aud (optional), Tx2Ctr, Rx2Aud, Rx2Ctr) from the first ($1^{st}$-WL) and second ($2^{nd}$-WL) communication links, respectively. The link control unit LCU is configured to repeatedly provide a second link quality measure LQ2 indicative of a link quality of the second communication link ($2^{nd}$-WL). The first and second hearing assistance devices are configured to exchange the respective second link quality measures (LQ2) between them via control signals Tx1Ctr/Rx1Ctr over the first communication link ($1^{st}$-WL). The first and second hearing assistance devices (HAD$_1$, HAD$_2$) each comprises a link quality unit (LQ) for extracting the second link quality measures (LQ2) indicative of a quality of the respective second communication links ($2^{nd}$-WL), the second link quality measures e.g. comprising a signal strength and/or a bit error rate of a signal received via the receiver (Rx2) from the auxiliary device (AD).

The link quality measures LQ2 are used to control the routing of audio signals transmitted by the auxiliary device (represented in FIG. 2 by transceiver unit Rx2/Tx2) as discussed in connection with FIG. 1A-B above and FIGS. 5A-5H below. In an embodiment, a measure of link quality (LQ2) is based on the signal strength of the received signal (e.g. based on the RSSI (received signal strength indication) and/or its bit error rate and/or the gain-settings of the receiver (e.g. of an automatic gain control (AGC) unit) of the receiving (or transmitting) device (forming part of the second wireless interface). In an embodiment, the binaural hearing assistance device is configured to forward information about a poor link quality measure (e.g. a received signal strength or a transceiver status) of a $2^{nd}$ communication link (e.g. $2^{nd}$-WL(2)) between the auxiliary device and one of the first or second hearing assistance devices (e.g. HAD$_2$) to the auxiliary device via (a back-link comprising) the first communication link (e.g. $1^{st}$-WL (21) and signals Tx1Ctr–>Rx1Ctr), the opposite hearing assistance device (e.g. HAD$_1$) and the second communication link (e.g. $2^{nd}$-WL(2) and signal Tx2Ctr) back to the auxiliary device (AD (Rx2/Tx2)).

Each of the hearing assistance devices (HAD$_1$, HAD$_2$) comprise an energy source status monitoring circuit (ESI) configured to monitor the current status of the local energy source (ES), e.g. a battery, via signal BatV, and to provide a corresponding energy status indication signal ESInd to the link control unit LCU. The energy status indication signals ESInd are exchanged between hearing assistance devices of the binaural hearing assistance system via the first communication link $1^{st}$-WL (signals Tx1Ctr–>Rx1Ctr). In each hearing assistance device, the energy status indication signal ESInd generated in and received from the opposite hearing assistance device is likewise fed to the link control unit LCU for evaluation (e.g. comparison with the locally generated energy status indication signal ESInd).

In an embodiment, at least one of the hearing assistance devices is configured to control the first ($1^{st}$-WL) and/or second ($2^{nd}$-WL) communication links dependent of the energy status indication signal(s) ESInd. In an embodiment, the binaural hearing assistance system BHAS is configured—in a specific power saving mode of operation where the energy status indication signal ESInd in the first hearing assistance device $HAD_1$ fulfils a predefined low status criterion—to relay an audio signal received from the auxiliary device AD by the second hearing assistance device $HAD_2$ to the first hearing assistance device $HAD_1$ via the first communication link 1st-WL(21) (signal Tx1Aud($HAD_2$)-> Rx1Aud($HAD_1$)).

Preferably, a predetermined priority (or priority algorithm) for weighting the influence of the link quality measure LQ2 and the energy status indication signal ESInd in the control of the first and/or second communication links.

The first and second hearing assistance devices ($HAD_1$, $HAD_2$) each comprise an input transducer IT and an output transducer OT, a forward path being defined therebetween and comprising a signal processing unit SPU for processing an input signal In comprising an audio signal and for providing an enhanced audio signal AIn. The enhanced audio signal AIn is fed to the link control unit LCU. In addition to determining an appropriate routing of the signals to and from the first and second communication links, the link control unit LCU is configured to provide a resulting audio signal AOut for being presented to the user via the output transducer OT. The resulting audio signal AOut may be one of an audio signal picked up by the input transducer (originating from signal In, AIn, e.g. comprising sounds from the environment), an audio signal received from the auxiliary device via the second communication link $2^{nd}$-WL (such signal originating from signal Rx2Aud), or a signal received from the other hearing assistance device via the first communication link $1^{st}$-WL (such signal originating from signal Rx1Aud), or a (e.g. weighted) mixture of two or more of these signals.

In an embodiment, the binaural hearing aid system BAHS further comprises second antenna and transceiver circuitry, allowing a second (RF) communication link between the first and second hearing assistance devices to be established. In an embodiment, such second communication link may be established by the antenna and transceiver units (Rx2/Tx2) for establishing second communication links ($2^{nd}$-WL) between the respective first and second hearing assistance devices ($HAD_1$, $HAD_2$) and the auxiliary device (AD). Alternatively, the first and second hearing assistance devices ($HAD_1$, $HAD_2$) each comprises separate antenna and transceiver units for establishing an interaural second (RF) communication link.

Preferably, the first and/or second communication links are configured to allow bi-directional transmission of control signals. Preferably, the first and/or second communication links are configured to allow bi-directional audio transmission ('duplex'). In an embodiment, the first and/or second communication links are configured to allow bi-directional audio transmission, but in one direction at a given time ('half duplex').

Various aspects of inductive (first) communication links are e.g. discussed in EP 1 107 472 A2, EP 1 777 644 A1, US 2005/0110700 A1, and US2011222621A1. WO 2005/ 055654 and WO 2005/053179 describe various aspects of a hearing aid comprising an induction coil for inductive communication with other units. A protocol for use in an inductive communication link is e.g. described in US 2005/ 0255843 A1.

In an embodiment, the (second) RF-communication link is based on classic Bluetooth as specified by the Bluetooth Special Interest Group (SIG) (cf. e.g. https://www.bluetooth.org). In an embodiment, the (second) RF-communication link is based other standard or proprietary protocols (e.g. a modified version of Bluetooth, e.g. Bluetooth Low Energy modified to comprise an audio layer).

Figure 3A:
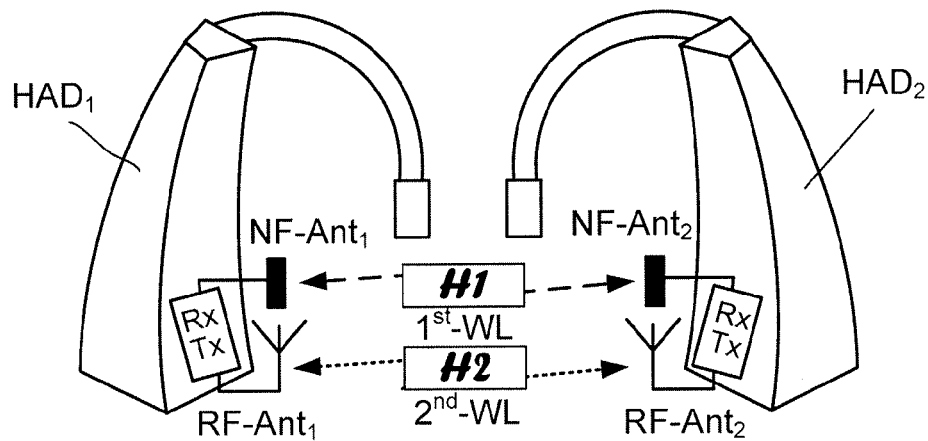
FIGS. 3A-3B show an embodiment of a binaural hearing aid system comprising first and second hearing assistance devices, the system being configured to determine whether or not the first and second hearing assistance devices are operationally mounted on the head of the user.
Figure 3B:
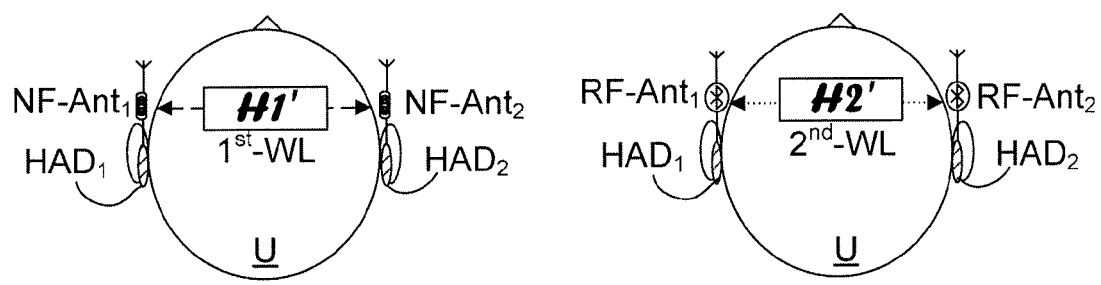

FIGS. 3A-3B show an embodiment of a binaural hearing aid system comprising first and second hearing assistance devices ($HAD_1$, $HAD_2$), the system being configured to determine whether or not the first and second hearing assistance devices are operationally mounted on the head of the user (U). FIG. 3A shows a situation, where the hearing assistance devices ($HAD_1$, $HAD_2$) are located close together, e.g. on a table or in a box. The first and second wireless interfaces comprise first ($NF-ANT_1$, $NF-ANT_2$) and second ($RF-ANT_1$, $RF-ANT_2$) sets of antennas, respectively, coupled to first and second transceiver circuitry (symbolically commonly denoted RxTx in each hearing assistance device). FIG. 3A illustrate the definition of the (current) transfer functions H1 and H2 for transmission between the first ($NF-ANT_1$, $NF-ANT_2$) and second ($RF-ANT_1$, $RF-ANT_2$) sets of antennas of the first ($1^{st}$-WL) and second ($2^{nd}$-WL) communication links, respectively, in this particular situation. FIG. 3B shows a (normal) operating situation of the system, where the hearing assistance devices ($HAD_1$, $HAD_2$) are mounted on the head of a user (here behind the ear). The left and right drawings of FIG. 3B illustrate the definition of the (reference) transfer functions H1' and H2' for transmission between the first ($NF-ANT_1$, $NF-ANT_2$) and second ($RF-ANT_1$, $RF-ANT_2$) sets of antennas of the first ($1^{st}$-WL) and second ($2^{nd}$-WL) communication links, respectively, in this normal mode of operation.

Hearing assistance devices ($HAD_1$, $HAD_2$) may be equipped with several wireless systems, such as e.g. magnetic inductance antennas (NF-Ant) and Bluetooth antennas (RF-Ant). Depending on the wireless technology used, the transfer function H between the antennas will be different. The transfer functions of the magnetic inductance antennas will mainly depend on the distance between the antennas, while the transfer function of the Bluetooth antennas will be affected by the energy loss inside the head of the user when the hearing assistance devices are mounted on the head of the user.

By transmitting a measure of the transmission power used by the transmitters of the first and second communication links ($1^{st}$-WL, $2^{nd}$-WL) of a given hearing assistance devices as a control signal to the opposite hearing assistance device, the transfer function between the two antennas of each link can be estimated in the receiving hearing assistance device. Knowledge about the transfer functions between the two of antennas of each set of antennas of the hearing assistance devices when mounted at each ear of a user, as shown in FIG. 3B (and their current values, where the devices may be arbitrarily located, e.g. operatively mounted or located close together on a table or in storage box (as shown in FIG. 3A), etc.) may be used to detect whether or not the hearing assistance devices are operationally mounted at each ear of the user. By combining (e.g. comparing) the estimated transfer functions (H1, H2) for the two different types of wireless interfaces (inductive ($1^{st}$-WL) and Bluetooth ($2^{nd}$-WL)) with respective reference values, an indication of the current location and environment of the hearing assistance devices, e.g. whether or not an RF-attenuating medium is located between the two devices. In an embodiment, the binaural hearing assistance system is configured to enter a power down mode, when the current values of the first and second transfer functions H1, H2 fulfill a predefined criterion e.g. H1>H1', H2>H2', where Hi' (i=1, 2) are the respective reference transfer functions, when operatively mounted on the user's head (as illustrated in FIG. 3B). Alternatively or additionally, the predefined criterion may comprise that H2>>H2', e.g. H2>5*H2', such as H2>10*H2', or H2>100*H2').

Figure 4:
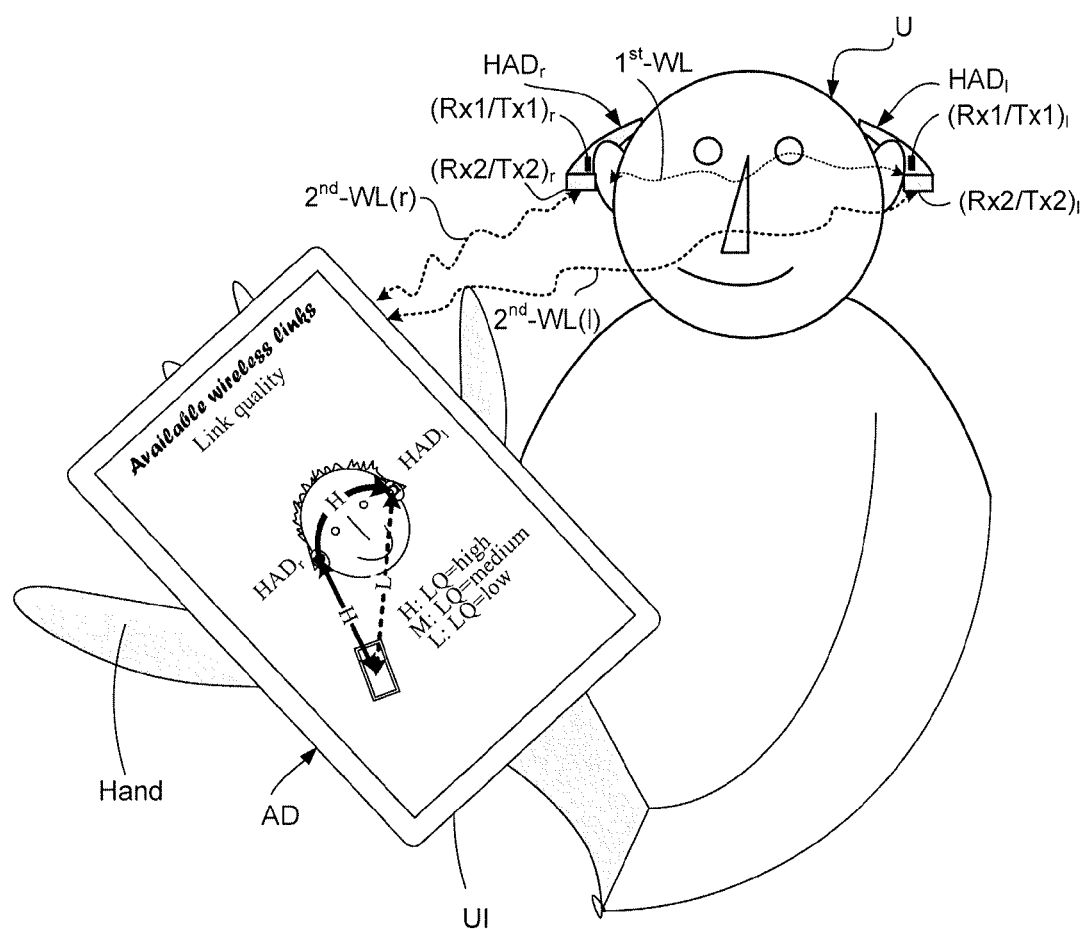
FIG. 4 shows an embodiment of a binaural hearing aid system comprising first and second hearing assistance devices in communication with an auxiliary device functioning as a user interface for the binaural hearing aid system.

FIG. 4 shows an embodiment of a binaural hearing aid system comprising left (second) and right (first) hearing assistance devices ($HAD_l$, $HAD_r$) in communication with a portable (handheld) auxiliary device (AD) functioning as a user interface (UI) for the binaural hearing aid system. In an embodiment, the binaural hearing aid system comprises the auxiliary device (and the user interface) and is configured to display the link quality measures estimated by the system. The user interface displaying the link qualities of the available wireless ($1^{st}$ and $2^{nd}$ communication) links of the binaural hearing aid system may be implemented as an APP of the auxiliary device (e.g. a SmartPhone). In the embodiment of FIG. 4, the available wireless links are denoted $1^{St}$-WL (inductive link between the hearing assistance devices) and $2^{nd}$-WL(l) and $2^{nd}$-WL(r) (RF-links between the auxiliary device and the left and between the auxiliary device and the right hearing assistance device, respectively). The $1^{st}$ and $2^{nd}$ wireless interfaces are implemented in the left and right hearing assistance devices ($HAD_l$, $HAD_r$) by antenna and transceiver circuitry Rx1/Tx1 and Rx2/Tx2, respectively. The auxiliary device comprising the user interface is adapted for being held in a hand (Hand) of a user (U), and hence convenient for displaying a current arrangement of available links and their estimated link qualities.

In an embodiment, threshold values of the first and second link quality measure LQ1 and LQ2 are defined (and e.g. stored in the respective link control units of the first and second hearing assistance devices), the respective threshold values $LQ1_{th,i}$ and $LQ2_{th,i}$ (i=1, 2, . . . , Q) being determined to separate different grades of link quality (e.g. a GOOD, BAD, Q=1, or GOOD, MEDIUM, BAD, Q=2) of the first and second communication links. In the example illustrated in FIG. 4, the (second) RF-link between the auxiliary device and the left hearing assistance device ($HAD_l$) has a low link quality (L, denoted L: LQ=low), whereas the (second) RF-link between the auxiliary device and the right hearing assistance device ($HAD_r$) has a high link quality (H, denoted H: LQ=high). The (first) inductive link between the left and right hearing assistance devices ($HAD_l$, $HAD_r$) is likewise indicated to have a high link quality (H). The first and second communication links are indicated to be bi-directional (by the double arrow). Typically, the first communication link is uni-directional audio (from one hearing assistance device to the other) and bi-directional control. Typically, the second communication links are uni-directional audio (from auxiliary device to hearing assistance device) and bi-directional control. In the example of FIG. 4, the medium link quality (M, denoted M: LQ=medium) is not used.

FIGS. 5A-5H show various configurations of the different wireless communications links of a binaural hearing assistance system according to the present disclosure. The binaural hearing assistance system comprises first and second hearing assistance devices ($HAD_1$, $HAD_2$) adapted to exchange audio and control signals (including link quality measures) between them via a first wireless interface enabling the establishment of a first communication link (denoted '1' in FIGS. 5A-5H) based on Near-Field (NF), e.g. inductive, communication. Each of the first and second hearing assistance devices ($HAD_1$, $HAD_2$) further comprises a second wireless interface enabling the establishment of a second communication link (denoted '2' in FIGS. 5A-5H) based on Far-Field communication (radiated fields (RF)) to an auxiliary device (AD). In FIGS. 5A-5H, the individual first and second communication link are illustrated as separate audio (bold line) and control (thin line) channels (typically one-way audio and two-way control channels). An inactive link (or a link with low or inferior transmission quality) is indicated in dashed line. Uni- and bi-directionality are indicated by arrows. Each of the first and second hearing assistance devices ($HAD_1$, $HAD_2$) and the auxiliary device (AD) comprise appropriate antenna and transceiver circuitry as necessary to implement the first and second communication links (and may e.g. be embodied as described in connection with FIG. 2). In FIGS. 5A-5H the antenna and transceiver circuitry is only indicated in the auxiliary device (denoted Rx/Tx), but implicit in the hearing assistance devices. In some embodiments, the first (1) and/or second (2, 2') communication links are configured to allow bi-directional audio transmission, transmission in both directions are enabled at a given time (sometimes termed 'duplex'). In some embodiments, the first (1) and/or second (2, 2') communication links are configured to allow bi-directional audio transmission, but in one direction at a given time (sometimes termed 'half duplex').

Figure 5A:
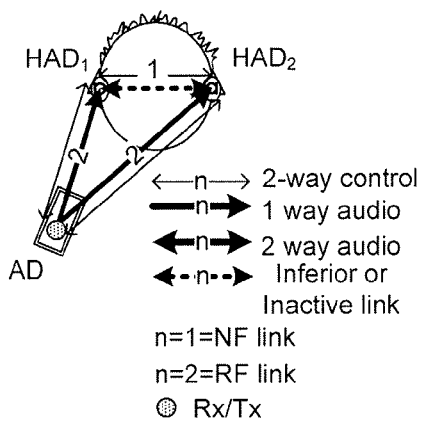
FIGS. 5A-5H show various configurations of the different wireless communications links of a binaural hearing assistance system according to the present disclosure.

FIG. 5A illustrates a normal situation where both of the second RF-links ('2') from the auxiliary device (AD) to the first and second hearing assistance devices ($HAD_1$, $HAD_2$) are active, whereas the inductive link ('1') between the first and second hearing assistance devices is deactivated (except for a control channel for bi-directional exchange of control signals). It may e.g. illustrate a situation where the same audio signal is streamed (broadcast) from the transceiver (Rx/Tx) of the auxiliary device (AD) (e.g. an entertainment device, e.g. a telephone) to the first and second hearing assistance devices ($HAD_1$, $HAD_2$). Second link quality measures (LQ2) representing estimates of the link qualities of the second RF-communication links to the respective first and second hearing assistance devices are exchanged between the hearing assistance devices on the 2-way control channel of the first inductive communication link.

Figure 5B:
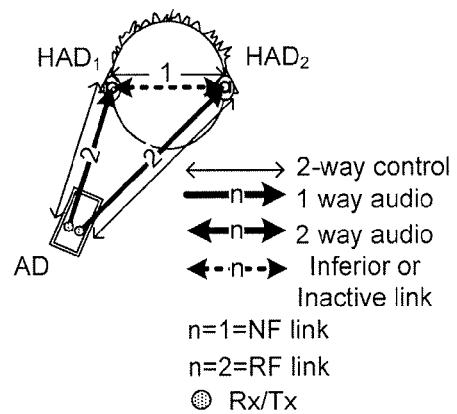

FIG. 5B illustrates a situation like the one described in FIG. 5A but where instead different audio signals are transmitted from the auxiliary device to the respective first and second hearing assistance devices ($HAD_1$, $HAD_2$). The scenario may e.g. represent a stereo signal being transmitted from the auxiliary device to the binaural hearing aid system. Alternatively, it may represent a situation where two independent audio signals are transmitted to the respective hearing assistance devices.

Figure 5C:
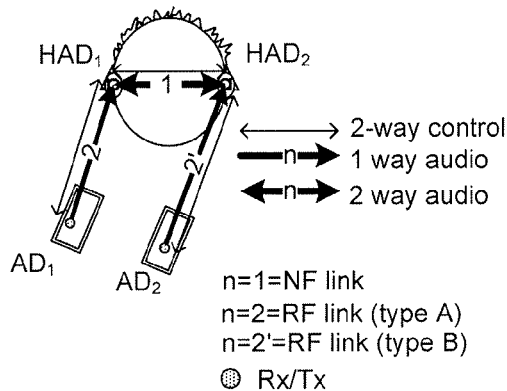

FIG. 5C illustrates a situation, where each of the first and second hearing assistance devices ($HAD_1$, $HAD_2$) is configured to establish a separate second RF-link (2, 2') to respective first and second auxiliary devices ($AD_1$, $AD_2$). In this setup, each of the first and second hearing assistance devices ($HAD_1$, $HAD_2$) may receive independent audio signals. The first hearing assistance device may e.g. receive a live transmission (e.g. from a telephone or a radio) from the first auxiliary device, and the second hearing assistance device may e.g. receive a recorded transmission (e.g. of music, or an audio book, etc.) from the second auxiliary device. The two separate second RF-links (2, 2') may implement wireless RF-interfaces according to the same specification (e.g. classic Bluetooth) or to different specifications (e.g. one according to classic Bluetooth, and one according to another standardized (e.g. DECT or Bluetooth Low Energy) or proprietary specification). The two, possibly independent, sources may be active at complementary points in time or be overlapping in time. The different audio signals received in the first and second hearing assistance devices ($HAD_1$, $HAD_2$) may be exchanged between the hearing assistance devices via the first inductive communication link (1). Thereby both devices have access to both audio signals, and hence, a combined (possibly a weighted combination) can be presented to the user at both ears (possibly differently weighted at the two ears).

In an alternative embodiment, the (single) auxiliary device AD contains two RF, e.g. Bluetooth (BT), transmitters (Rx/Tx). One transmitter sends the signal to the first hearing assistance device (e.g. HAW using a first BT-channel (2); the second transmitter sends the same signal by a different BT-channel (2') to the other hearing assistance device (e.g. $HAD_2$). In this embodiment, the hearing assistance devices are configured to interchange the two received signals (and/or link quality measures of the respective BT-links/channels (2, 2')) via the first (inductive) communication link (1). Hence, the signal with the best quality can be presented at both ears (either a) as determined in each hearing assistance device separately, based on the received versions of the signal transmitted from the auxiliary device, or b) by comparison of link quality measures for the two BT-channels at the given point in time; and subsequently transfer of the signal with the best quality to the respective other device). The advantage would be that the two transmission channels (2, 2') are not necessarily jammed by the same amount of noise (at a given time), whereby the probability of receiving a signal of sufficient quality at both hearing assistance devices is increased.

In an embodiment, the binaural hearing assistance system is arranged to provide that both hearing assistance devices ($HAD_1$, $HAD_2$)—at the same time—may transmit different signals to an auxiliary device (AD) via respective RF and/or inductive communication links. This requires e.g. that the auxiliary device (AD) comprises two different RF (e.g. BT) receivers or one RF and one inductive receiver (or two inductive receivers).

In another embodiment of a system comprising two auxiliary devices, each of the auxiliary devices comprise a microphone. In this scenario such microphones could be used to pick up sound from two independent audio sources (e.g. two different speakers, e.g. to aid a hearing impaired person in a conversation with two different persons in a noisy environment, e.g. a restaurant). In an embodiment, at least one of the two (such as both) auxiliary devices each comprise a SmartPhone configured to be used as an external microphone for the hearing assistance devices.

Figure 5D:
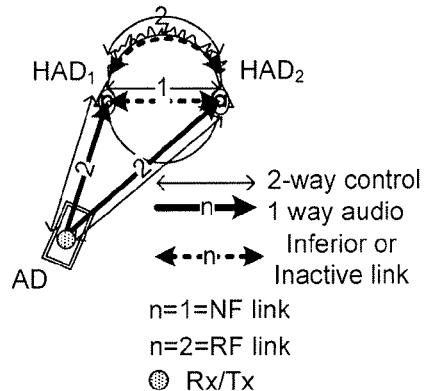

FIG. 5D illustrates a scenario as described in connection with FIG. 5A, but where additionally or alternatively, an RF-link between the first and second hearing assistance devices ($HAD_1$, $HAD_2$) can be established. The interaural RF-link may be used to exchange control signals or—if convenient in a given situation audio signals between the first and second hearing assistance devices. In the embodiment shown in FIG. 5D the audio channels of the interaural links between the first and second hearing assistance devices ($HAD_1$, $HAD_2$) are deactivated, whereas the (bi-directional) control channels are active. In an embodiment, the same (duplicate) data can be exchanged on the two links to increase reliability. Alternatively, different data can be exchanged on the two links, e.g. link quality data on one link and other data on the other. In an embodiment, data are transmitted and distributed on the two links depending on the current bandwidth requirements. In an embodiment, control data are exchanged between the first and second hearing assistance devices ($HAD_1$, $HAD_2$) on the inductive link (1), whereas audio data are exchanged between first and second hearing assistance devices on the RF-link (2).

Figure 5E:
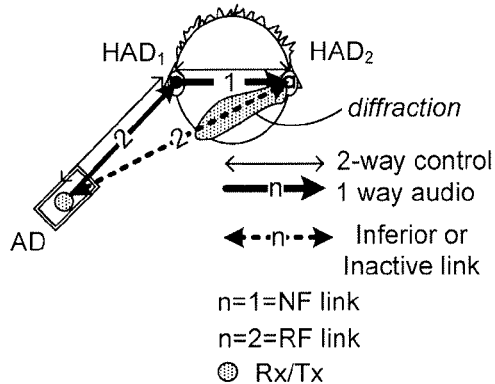

FIG. 5E illustrates a situation where the link quality of the RF-link (2) from the auxiliary device (AD) to the second hearing assistance device ($HAD_2$) is inferior, here due to attenuation of the RF-signal due to the presence of a diffractive medium (here the user's head, as indicated in FIG. 5E by the shaded area denoted diffraction) in the transmission path between the auxiliary device and the second hearing assistance device). The binaural hearing assistance system is configured to (e.g. automatically, based on the link quality measures LQ2 of the RF-links) reconfigure the communication links, so that the audio signal received at the first hearing assistance devices (HAW via RF-link (2) from the auxiliary device (AD) is relayed to the second hearing assistance device ($HAD_2$) via the interaural inductive link (1). Thereby the audio signals can be presented to the user at both ears even though one of the RF-links from the auxiliary device is inferior.

Figure 5F:
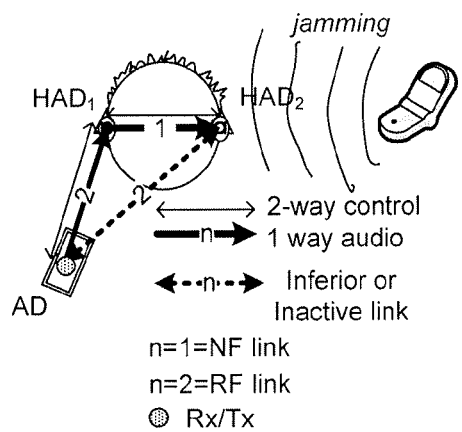

FIG. 5F illustrates a situation similar to the one in FIG. 5E, but where the inferior link quality of the RF-link (2) from the auxiliary device (AD) to the second hearing assistance device ($HAD_2$) is due to jamming of the RF-signal to the second hearing assistance device ($HAD_2$), e.g. from a portable communication device, e.g. a cellular telephone. The reaction of the binaural hearing assistance system is the same as in the scenario of FIG. 5E.

Figure 5G:
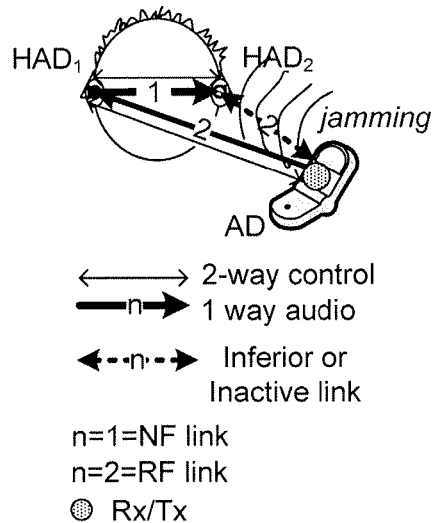

FIG. 5G illustrates a situation similar to the one in FIG. 5F, but where the auxiliary device itself (AD), here a cellular telephone, jams the second transceiver circuitry in the second hearing assistance device ($HAD_2$) (too close to the transmitter of the cellular telephone), thereby prohibiting the device from receiving the audio signal from the cellular telephone. In the scenario of FIG. 5G, the RF-link (2) from the cellular telephone (AD) to the first hearing assistance device (HAW is functional and the binaural hearing assistance system is configured to relay the audio signal received in the first hearing assistance device to the second first hearing assistance device via the interaural inductive link (1).

Figure 5H:
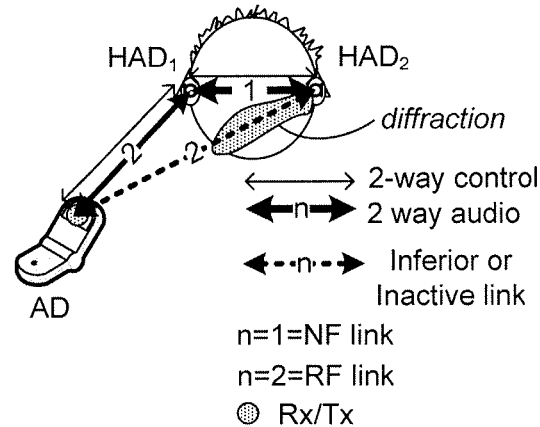

FIG. 5H illustrates a situation, where audio signals from the hearing assistance devices(s) ($HAD_1$, $HAD_2$) (e.g. picked up by a microphone of the hearing assistance devices(s)) are transmitted to the auxiliary device(s) (AD), here illustrated as a cell phone. This scenario may reflect a telephone conversation, where the user's voice is picked up by microphones of the hearing assistance devices and transmitted 'back' to the cell phone via the second communication link(s) (2). In this scenario, the second (RF) communication links are configured to be bi-directional (duplex) links. In the illustrated example, a situation as also described in connection with FIG. 5E, prevails. Here, the $2^{nd}$ RF-link (2) from the cell phone to the second hearing assistance device ($HAD_2$) is inferior (e.g. due to shadowing effect of the user's head, diffraction in FIG. 5H). Consequently, the binaural hearing assistance system is configured to transmit (relay) audio signals received by the first hearing assistance device (HAW from the cell phone (AD) to the second hearing assistance device ($HAD_2$) on the first (inductive) communication link (1). Further, the system is configured to transmit the microphone signal picked up by the second hearing assistance device (HAD$_2$) to the first hearing assistance device (HAD$_1$) via the 1$^{st}$ inductive link (1), where it e.g. is mixed with a microphone signal picked up by a microphone of the first hearing assistance device (HAD$_1$). A resulting, mixed microphone signal is transmitted (back) to the cell phone (AD) via the 2$^{nd}$ RF-link from the first hearing assistance device (HAD$_1$).

Figure 6A:
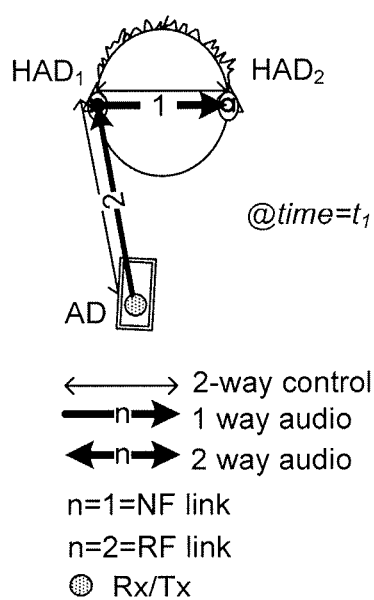
FIGS. 6A-6B show embodiments of a binaural hearing assistance system comprising first and second hearing assistance devices in communication with an auxiliary device, where the transmission of audio signals from the auxiliary device to the first and second hearing assistance devices alternatingly uses the $2^{nd}$ communication link to the first and second hearing assistance devices (one at a time) and the $1^{st}$ communication link to relay the audio signal to 'the other' hearing assistance device.
Figure 6B:
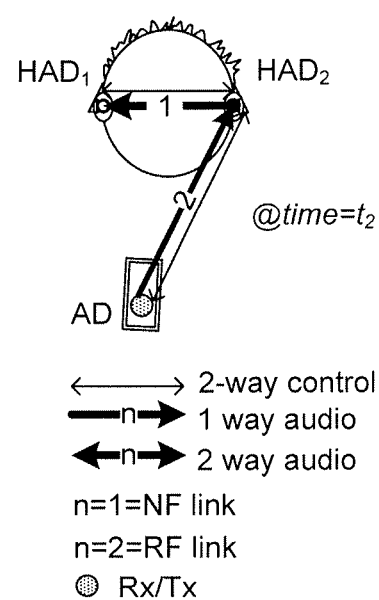

FIGS. 6A-6B schematically show embodiments of a binaural hearing assistance system comprising first and second hearing assistance devices (HAD$_1$, HAD$_2$) in communication with an auxiliary device (AD) implementing a specific power saving mode of operation. In this power saving mode of operation, the binaural hearing assistance system is adapted to transmit audio signals from the auxiliary device (AD) to the first and second hearing assistance devices (HAD$_1$, HAD$_2$) by alternatingly using the 2$^{nd}$ communication link (2) to the first and second hearing assistance devices (one at a time), respectively, and continuously using the 1$^{st}$ communication link (1) to relay the audio signal to 'the other' hearing assistance device. In the specific power saving mode of operation, only one of the second communications links (2) between an auxiliary device (AD) and a hearing assistance device (HAD$_1$ or HAD$_2$) is actively receiving audio (or is active at all) at a given time. FIGS. 6A and 6B illustrates the two possible configurations of the system in the specific power saving mode. FIG. 6A corresponds to a first point in time t$_1$ (denoted @time=t$_1$ in FIG. 6A), where the second communication link to the first hearing assistance device (HAW is active. FIG. 6B corresponds to a second point in time t$_2$ (denoted @time=t$_2$ in FIG. 6B), where the second communication link to the second hearing assistance device (HAD$_2$) is active. The binaural hearing assistance system may e.g. be configured to switch between the first and second hearing assistance device as the sole recipient of an audio signal via the second communication link with a predefined switch frequency, e.g. every hour, and/or controlled by a user via a user interface and/or in connection with a power-up after a power-down.

FIGS. 7A-7C show embodiments of an auxiliary device functioning as a user interface for a binaural hearing aid system according the present disclosure, FIGS. 7A, 7B and 7C illustrating three different audio routing scenarios between the auxiliary device and the hearing assistance devices, such routing being selectable via the graphical user interface of the auxiliary device (e.g. based on link quality measures illustrated in the display).

The user interface is implemented in the auxiliary device, e.g. as a remote control device, e.g. implemented as an APP, e.g. as an APP of a SmartPhone, from which a user can select a suitable routing of an audio signal from the auxiliary device to each of the first and second hearing assistance devices. The auxiliary device comprises a graphical interface (e.g. a touch sensitive display) allowing a user to control the 1$^{st}$ and 2$^{nd}$ communication links by activating or deactivating a link in the current arrangement of devices (e.g. by clicking on different parts of the arrowed lines representing the 1$^{st}$ and 2$^{nd}$ communication links in the display). Preferably, the estimated current audio link quality (LQ) of the audio links are illustrated via the graphical user interface, cf. indications H, M, L, indicating a high, a medium, and a low link quality, respectively (as also described in connection with FIG. 4). This indication may be utilized to manually override an automatic routing strategy implemented in the hearing assistance system. In an embodiment, the estimated current audio link quality of at least the 2$^{nd}$ communication links from the auxiliary device to the hearing assistance devices are indicated. Preferably, the estimated current audio link qualities in both directions of the 1$^{st}$ communication link between the hearing assistance devices are included as well. It is to be understood that the activation or deactivation of the 1$^{st}$ communication link is intended to only concern the audio signal part of the transmitted signal. In general, the control signal part of the 1$^{st}$ communication link, including the link quality measures (LQ2 and optionally LQ1(HAD$_l$->HAD$_r$) and LQ1(HAD$_r$->HAD$_l$) exchanged between the two hearing assistance devices (HAD$_l$, HAD$_r$) is intended to be always on (at least in an audio reception mode where audio signals are to be received from the auxiliary device).

A given audio link can be activated (or deactivated) by clicking on a central part of the bold line representing the link in question. A direction of transmission can be selected (or deselected) by clicking on an end of the line representing the link in question. FIGS. 7A-7C show examples of possible routing scenarios. FIG. 7A shows a situation where the audio link to the left hearing assistance device (HAD$_l$) is deactivated (having a low estimated link quality L), so the audio signal to the left hearing assistance device (HAD$_l$) is provided by the RF-link to the right hearing assistance device (HAD$_r$) (having a high estimated link quality H), and relayed further by the inductive link to the left hearing assistance device (HAD$_l$). FIG. 7B shows a situation (e.g. a test scenario) where the audio link to the right hearing assistance device (HAD$_r$) is deactivated (having a high estimated link quality H), so the audio signal to the right hearing assistance device (HAD$_r$) is provided by the RF-link to the left hearing assistance device (HAD$_l$) (having a low estimated link quality L) and further by the inductive link to right hearing assistance device (HAD$_r$). FIG. 7C shows a situation (e.g. a normal scenario) where both of the RF-links to the left and right hearing assistance devices (HAD$_l$, HAD$_r$) (both having a high estimated link quality H) are active, whereas the inductive link between the left and right hearing assistance devices is deactivated (except for control signals). Thereby routing of audio signals between an auxiliary device and a pair of hearing assistance devices can be controlled according to a user's wishes via the user interface.

In the embodiment of FIGS. 7A-7C, the user interface is assumed to form part of the auxiliary device that also provides the audio signal (e.g. integrated in a SmartPhone or tablet computer or a music delivery device). Alternatively, the user interface and the audio signal delivery device may be implemented in two different devices, e.g. a remote control (user interface) and a TV-set (audio source), respectively.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims and equivalents thereof.

REFERENCES

US2008159548A1 (STARKEY) 3 Jul. 2008
US2007291970A1 (SAT) 20 Dec. 2007
EP1107472A2 (SONY) 13 Jun. 2001
EP1777644A1 (OTICON) 24 May 2007
US20050110700A1 (STARKEY/OTICON) 26 May 2005
US2011222621A1 (OTICON) 15 Sep. 2011
WO2005055654 (STARKEY/OTICON) 16 Jun. 2005

WO2005053179 (STARKEY/OTICON) 9 Jun. 2005
US20050255843A1 (STARKEY/OTICON) 17 Nov. 2005.

The invention claimed is:

1. A binaural hearing assistance system comprising first and second hearing assistance devices adapted for being located at or in or fully or partially implanted in the head at left and right ears of a user, wherein each of the first and second hearing assistance devices comprises
   a) a first wireless interface comprising first antenna and transceiver circuitry adapted for establishing a first communication link to the respective other hearing assistance device based on near-field communication;
   b) a second wireless interface comprising second antenna and transceiver circuitry adapted for establishing a second communication link to an auxiliary device based on far-field communication;
   c) an energy source,
   d) an energy source status monitoring circuit configured to monitor a current status of the energy source and provide an energy status indication signal,
   e) a link control unit operatively coupled to the energy source status monitoring circuit, and the link control unit is further operatively coupled to the first antenna and/or the second antenna and transceiver circuitry, and
   wherein the first and second hearing assistance devices are configured to transmit the energy status signals via the second communication link to an auxiliary device and/or exchange the energy status signals via the first communication link.

2. A binaural hearing assistance system according to claim 1, wherein the link control unit is configured to exchange the energy status signals between the first and second hearing assistance devices via the first and/or second communication links.

3. A binaural hearing assistance system according to claim 1, wherein at least one of the hearing assistance devices is configured to control the first and/or second communication link dependent on the respective energy status indication signal(s).

4. A binaural hearing assistance system according to claim 1 configured to:
   a specific power saving mode of operation where the energy indication signal in the first hearing assistance device fulfills a predefined low status criterion,
   relay an audio signal received from the auxiliary device by the second hearing assistance device to the first hearing assistance device via the first communication link.

5. A binaural hearing assistance system according to claim 4, wherein the low status criterion comprises that the energy status indication signal is below a threshold value of the energy status indication signal, or that a numerical difference between energy status indication signals of the first and second hearing assistance devices is above a predefined difference value.

6. A binaural hearing assistance system according to claim 4 in the specific power saving mode of operation is configured to alternatingly select the hearing assistance device that receives the audio signal from the auxiliary device and relays the audio signal to the other hearing assistance device via the first communication link as the first and second hearing assistance device, respectively, so that only one of the second communication links between the auxiliary device and a hearing assistance device is actively receiving audio or active at all at a given time.

7. A binaural hearing assistance system according to claim 4 is configured to switch between the first and second hearing assistance device to receive the audio signal via the second communication link with a predefined frequency and/or controlled by a user via a user interface.

8. A binaural hearing assistance system according to claim 1, wherein the link control unit is configured to repeatedly provide a second link quality measure indication of a link quality of the second communication link, and wherein the first and second hearing assistance devices are configured to exchange the second link quality measures between them via the first and/or second communication links.

9. A binaural hearing assistance system according to claim 8, wherein the link control unit is configured to give a different priority to the link quality measures than to the energy status indication signal during control of the first and/or second communication links to ensure that high quality second communication link is not powered down due to power consumption considerations.

10. A binaural hearing assistance system according to claim 1 wherein the energy status indication signal is indicative of a rest capacitive of the energy source, an estimate time before exchange or charge the energy source.

11. A binaural hearing assistance system according to claim 1 wherein the energy status indication signals are repeatedly provided to indicate a current status of the energy source.

12. A binaural hearing assistance system according to claim 1 wherein said first communication link is an inductive link.

13. A binaural hearing assistance system according to claim 1 wherein said second communication link is based on Bluetooth technology.

14. A binaural hearing assistance system according to claim 1 wherein the first and second hearing assistance devices are adapted to establish the second communication link to the auxiliary device according to different standardized or proprietary wireless communication technologies.

15. A method of operating a binaural hearing assistance system comprising first and second hearing assistance devices adapted for being located at or in or fully or partially implanted in left and right ear regions of a user, the method comprising in each of the first and second hearing assistance devices
   a) providing a first wireless interface adapted for establishing a first communication link to the respective other hearing assistance device based on near-field communication;
   b) providing a second wireless interface adapted for establishing a second communication link to an auxiliary device based on far-field communication;
   c) providing an energy source;
   d) providing an energy source status monitoring circuit configured to monitor a current status of the energy source and provide an energy status indication signal,
   e) providing a link control unit operatively coupled to the energy source status monitoring circuit, and the link control unit is further operatively coupled to the first antenna and/or the second antenna and transceiver circuitry, and
   in the binaural hearing assistance system,
   transmitting the energy status signals via the second communication link to an auxiliary device, and/or
   exchanging the energy status signals via the first communication link.

16. A data processing system comprising a processor and program code means for causing the processor to perform the method of claim 15.

17. A binaural hearing assistance system according to claim 1 wherein the auxiliary device is or comprises a cell phone.

\* \* \* \* \*